(12) United States Patent
Rasmussen et al.

(10) Patent No.: US 6,624,270 B1
(45) Date of Patent: Sep. 23, 2003

(54) COPOLYMERS DERIVED FROM VINYL DICYANOIMIDAZOLES AND OTHER MONOMERS

(75) Inventors: Paul G. Rasmussen, Ann Arbor, MI (US); David M. Johnson, Ann Arbor, MI (US); Nagash A. Clarke, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/483,608

(22) Filed: Jan. 14, 2000

(51) Int. Cl.[7] .................................................. C08F 26/06
(52) U.S. Cl. ..................... 526/258; 526/262; 526/263; 526/347.1; 526/341; 526/335; 526/319
(58) Field of Search .................... 526/262, 258, 526/263, 347.1, 341, 335, 319

(56) References Cited

U.S. PATENT DOCUMENTS

| | | |
|---|---|---|
| 2,534,331 A | 12/1950 | Woodward |
| 3,778,446 A | 12/1973 | Weigert |
| 3,806,517 A | 4/1974 | Begland |
| 4,097,475 A | 6/1978 | James |
| 4,220,466 A | 9/1980 | Patel |
| 4,299,939 A | 11/1981 | Panzer |
| 4,410,706 A | 10/1983 | Rothenberg |
| 4,585,724 A | 4/1986 | Helling |
| 4,600,681 A | 7/1986 | Bergthaller |
| 5,021,540 A | 6/1991 | Leone-Bay |
| 5,122,563 A | 6/1992 | Kaminski |
| 5,523,008 A | 6/1996 | Boden |
| 5,646,296 A | 7/1997 | Ippoliti et al. |
| 5,663,126 A | 9/1997 | Boden |
| 5,674,436 A | 10/1997 | Breitenbach |
| 5,677,384 A | 10/1997 | Detering |
| 5,712,408 A | 1/1998 | Rasmussen |
| 6,096,899 A * | 8/2000 | Rasmussen et al. ...... 548/312.7 |

FOREIGN PATENT DOCUMENTS

| | | |
|---|---|---|
| DE | 44 29 464 a | 2/1996 |
| EP | 0 042 938 A | 1/1982 |
| JP | SHO 49-134676 | 12/1974 |
| WO | WO 96 26229 A | 8/1996 |

OTHER PUBLICATIONS

P.S. Robertson and J. Vaughan, "Derivatives of the Hydrogen Cyanide Tetramer: Structure and Chemistry," (Dept. of Chemistry, University of Canterbury), Jun. 5, 1958, 2691–2693.

Yoshitaka Yamada, Izumi Kumashiro and Tadao Takenishi, "Synthesis of 4,5–Di– and 1,4,5–Trisubstituted Imidazole Derivatives from 4,5–Dicyanoimidazole," Bulletin of the Chemical Society of Japan, vol. 41, 1237–1240 (1968).

D.S. Donald and O.W. Webster, "Synthesis of Heterocycles from Hydrogen Cyanide Derivatives," Advances in Hererocyclic Chemistry, vol. 41, 6–9 (1987).

Herman F. Mark, Norbert M. Bikales, Charles G. Overberger, Georg Menges, and Jacqueline I. Kroschwitz, Encyclopedia of Polymer Science and Engineering, vol. 12, "Polyesters to Polypeptide Synthesis," 346–347 (1988).

(List continued on next page.)

Primary Examiner—David W. Wu
Assistant Examiner—William K Cheung
(74) Attorney, Agent, or Firm—Harness, Dickey & Pierce, PLC

(57) ABSTRACT

A copolymer comprising imidazole ring units having nitrogen at the 1 and 3 positions of the ring; a carbon at each of the 2, 4 and 5 positions of the ring; and radical substituents G1 and G2 carried at the 4 and 5 positions together with a non-imidazole monomer capable of undergoing addition polymerization. In the imidazole, G1 and G2 are each independently selected from cyano, substituents derived from cyano, and substituents which replace cyano. The invention also provides a method for using the co-polymers as a coupling/activator for synthon synthesis.

6 Claims, 21 Drawing Sheets

OTHER PUBLICATIONS

David S. Allan, Ernest L. Thurber and Paul G. Rasmussen, "Polymers Containing Cyanoimidazole Pendant Groups", Journal of Polymer Science: Part A: Polymer Chemistry, vol. 28, 2475–2483 (1990).

PCT Search Report, Nov. 25, 1997, PCT/US97/14039 (Aug. 8, 1997).

Chemical Abstracts, vol. 82, No. 25, Jun. 23, 1975, Columbus, Ohio, US, Abstract No. 170924q.

Chemical Abstracts, vol. 83, No. 24, Dec. 15, 1975, Columbus, Ohio, US, Abstract No. 195237B.

Chemical Abstracts, vol. 126, No. 20, May 19, 1997, Columbus, Ohio, US, Abstract No. 264400v.

WO 97/14706; Wolfgang Pieken et al; Apr. 24, 1997.

WO 97/14710; George Just et al; Apr. 24, 1997.

Marvin H. Caruthers, "Gene Synthesis Machines: DNA Chemistry and Its Uses," Journal of Chemical Education, vol. 230, Oct. 1985, 281–285.

Marvin H. Caruthers, "Chemical Synthesis of DNA," Concepts in Chemistry, Journal of Chemical Education, vol. 66, No. 7, Jul. 1989, 577–580.

M.D. Matteucci and M.H. Caruthers, "The Synthesis of Oligodeoxypyrimidines on a Polymer Support," Tetrahedron Letters, vol. 21, pp. 719–722, Pergamon Press Ltd., Great Britain (1980).

Robert L. Letsinger and V. Mahadevan, "Stepwise Synthesis of Oligodeoxyribonucleotides on an Insoluble Polymer Support," Journal of the American Chemical Society, 88:22, Nov. 20, 1966, pp. 5319–5324.

Theophil Eicher, Dieter Lerch: "Zur Reaktionsweise des 3–Ethoxy–1,2–Diphenyl–Cyclopropenyliumkati ons mit bifunkzionellen aromatischen Aminen" Tetrahedron Letters, vol. 21, 1980, pp. 3751–3754, XP002102685.

* cited by examiner

COPOLYMERS DERIVED FROM VINYL DICYANOIMIDAZOLES AND OTHER MONOMERS

FIELD OF THE INVENTION

The present invention relates to compounds and copolymers based on and formed from substituted imidazoles, particularly from vinyl dicyanoimidazoles and methods of preparing such copolymers. More particularly, the present invention pertains to copolymers which incorporate 4,5-dicyano-2-vinylimidazole and its derivatives.

BACKGROUND OF THE INVENTION

Vinyl dicyanoimidazoles are a family of substituted imidazole compounds which can be made from the oxidation of reaction products synthesized by carefully controlled Schiff base reactions of diaminomaleonitrile (DAMN) with several conjugated aldehydes. Vinyl dicyanoimidazoles and their derivatives can polymerize to form homopolymers which exhibit desirable characteristics such as elevated glass transition temperature and flammability resistance. Incorporation of vinyl dicyanoimidazoles and derivatives thereof into copolymerized materials with various existing monomeric compounds would be desirable but, heretofore has not been accomplished.

To date, various copolymer-forming methodologies exist. Formulation of copolymers from unsubstituted imidazoles is discussed in the work of K. L. Petrak, Journal of Polymer Science: Polymer Letters Edition, 16, 393–399 (1978). However, unsubstituted imidazoles behave very differently from 4,5 dicyano substituted imidazoles. For example, proton acidities differ by nine orders of magnitude due to significant differences in polarity and available resonance structures.

Predictions regarding which monomers will react together successfully to form copolymers is difficult to do with consistency and accuracy. Prediction has been attempted by several methods. The best known method, often called the Q-e scheme is due to Alfrey and Price and is described in standard reference texts such as Odian, *Principles of Polymerization, $3^{rd}$Edition,* Wiley-Interscience 1991, at pages 489–91. In the Q-e scheme, an attempt is made to correlate the resonance (Q) and polarity factors (e) of the monomers with their behavior in copolymerization. Empirically, it has been found that monomers of very different Q's copolymerize poorly. However, the precision or accuracy of the available Q and e values is often poor. Thus, correlation is generally successful in hindsight, but has proven to be of limited predictive value. Thus successful copolymerization of various monomers with substituted imidazoles would not be easily predicted from the technology as it existed heretofore.

Presently there is a need for copolymers which retain many of the advantageous characteristics of homopolymeric compositions but exhibit enhanced thermal stability and flame retardance, for example. In spite of a great many efforts and much desire, it is difficult to bring new monomers and polymers into the high volume market due, in part, to high capital costs and stringent controls over feedstocks and processing. Thus, the ability to identify and incorporate various loadings of a monomer or comonomer into a copolymeric matrix to effect performance improvement at low cost is highly desired. It is also desirable that the resulting copolymer be thermally robust, and be capable of forming stable coatings.

SUMMARY OF THE INVENTION

It is an object of the present invention to provide novel copolymers which incorporate substituted imidazoles, particularly cyano-substituted imidazoles into the respective copolymeric matrix. The substituted imidazole contemplated in the present invention may be incorporated as either a monomer or homopolymer. It is also contemplated that the substituted imidazole which may be incorporated is a copolymeric material.

More particularly, it is an object of the present invention that the compound which may be incorporated is a 4,5-dicyano-2-vinylimidazole (also referred to hereafter as "VINAZENE™") or derivatives thereof; present initially as a monomer or homopolymer. It is also contemplated that the VINAZENE™ or VINAZENE™ derivative which is incorporated may be present initially as a copolymer with other compounds deemed useful to the make-up of the final copolymeric compound.

It is a further object of the present invention that the VINAZENE™ or VINAZENE™ derivatives be polymerizable with various standard monomers to form novel copolymers, terpolymers and the like. The various 4,5-dicyano-2-vinylimidazoles which can be employed in the present invention are, preferably, those having the formula as per FIG. 1 in which R1 is characterized as being hydrogen or an organic substitute which does not interfere with polymerization and/or copolymerization and is attachable to the cycle compound by an electrophilic agent.

It is also an object of this invention to provide processes and methods whereby VINAZENE™ and VINAZENE™-derivatives can copolymerized to form novel and enhanced polymeric material. Further objects of the present invention will become apparent in reading the specification of the present invention.

Generally speaking, the present invention is directed to new polymeric materials in which substituted imidazoles, namely vinyl dicyanoimidazoles, are incorporated into a copolymeric or terpolymeric matrix with various known monomers. Specifically, the copolymer or terpolymeric matrix contemplated in the present invention will contain 4,5-dicyano-2-vinylimidazole (VINAZENE™) or derivatives thereof, with 1-alkyl derivatives having 1 to 12 carbon atoms being particularly favored. The other monomers employed in the copolymeric matrix may be any monomeric compound which typically is capable of undergoing copolymerization reactions, with monomers capable of undergoing addition polymerization being particularly favored. Such monomers include, but are not limited to conjugated dienes such as styrene, styrene derivatives, isoprene, butadiene, chloroprene and, cyclopentadiene, substituted acrylate esters, alkyl acrylate esters and methacrylates, with methyl methacrylate being particularly preferred. Other materials which can be employed as monomers include materials such as acrylonitrile or other vinylic monomers. It is to be understood that the foregoing list is deemed to be illustrative of suitable monomers rather than imitative of the present invention.

DESCRIPTION OF THE PREFERRED EMBODIMENT

The present invention is based upon the unexpected discovery that members of the newly discovered class of compounds, substituted imidazoles, can be employed in copolymerization processes with various conventional monomeric and polymeric feed stock materials to yield novel copolymers in which targeted properties or characteristics are advantageously moderated or "tuned". The substituted imidazoles which are particularly favored are vinyl substituted ring compounds and alkyl derivatives thereof. The particular compounds which can be advantageously employed to this end are 4,5-dicyano-2-vinylimidazoles (VINAZENE™) and derivatives thereof. Among VINAZENE™ derivatives, the 1-alkyl derivatives having 1 to 12 carbon atoms are preferred, with compounds such as 1-methyl-VINAZENE™ and 1-ethyl-VINAZENE™ being most preferred.

Figure 1:
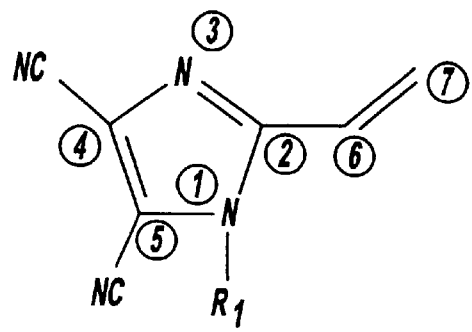
FIG. 1 is an illustration of a cyclic 2-vinyl imidazole compound with $R_1$ preferably, being hydrogen or a substituted or unsubstituted alkyl or a substituted or unsubstituted aryl having one to twelve carbon atoms.

Substituted imidazole ring compounds have a general formula as shown in FIG. 1. In the formula depicted in FIG. 1, R1 may be hydrogen or an organic substituent that does not interfere with polymerization. In the case of anionic polymerization, R1 is an organic substituent that does not contain an acidic proton and does not interfere with polymerization. In another aspect, R1 is an organic substituent attachable to the cyclic ring structure by an electrophilic agent. It is preferred that R1 is a substituted or unsubstituted alkyl having 1 to 12 carbon atoms. It is most preferred that R1 is selected from the group consisting of methyl, ethyl, propyl, isobutyl, benzyl, nonyl, and carbomoyl. The aforesaid selection criteria for the organic substituent requires that it be sterically non-hindering, so that the organic substituent is sterically non-hindering upon polymerization. It should be noted that the terms "organic radical", "organic group", and "organic substituent" are used herein interchangeably. The substituent carried on the 1-nitrogen position may be more generally represented as E, which is any substituent, and preferably is attachable to the nitrogen by an electrophilic agent, and is not necessarily hydrogen or organic. It is contemplated that E may be a catalytically active group which renders the material useful as a catalytic agent. It is also contemplated that E may be a flourescent group in which has utility for assay purposes E may be a hydrophobic modifier or may be a cross-linking agent that is a bifunctional electrophile or bifunctional epoxide.

One advantageous feature of the invention is the broad range of the substituent, E or R1, on the 1-N of 2-vinyl-4, 5-dicyanoimidazole; and the role of E or R1 on the polymer derived from the above monomer. The location of E, R1 on the monomer makes it unlikely that even moderately bulky groups will interfere with the vinylic polymerization by either free radical or anionically induced polymerization. Thus, R1 can be nearly any organic group which can be put on by reaction with an electrophilic reagent In some cases, R1 might be chosen to afford certain solubility characteristics to the polymer. For example, if R1 is a relatively long chain such as nonyl, the polymer would be solubilized in the less polar organic solvents. If R1 is a small group such as methyl, its steric influence on polymer properties and backbone would be minimized. It is noteworthy that the presence of any group R1 makes the molecule behave differently from 1-H because of the acidity of the H. Attempts to polymerize 2-vinyl-4,5-dicyanoimidazole by anionic methods would lead to deprotonation and no addition polymerization. The thermal polymerization of 1-H-2-vinyl-4,5-dicyanoimidazole is a special case and is described separately.

In some cases, R1 could be chosen because of its ease of removal. However, unlike the protecting groups commonly employed on imidazoles, dicyanoimidazoles are not well protected by silylation or acylation. Silyl groups or acyl groups come off too readily. Additional protecting groups which may be useful in various applications are ethyl, isopropyl, sec-butyl, benzyl, methoxybenzyl, methyloxymethyl, carbamoyl, etc.

After polymerization and deprotection of the 1-N, this site is again available for functionalization. A variety of electrophiles could be chosen to attach groups which provide specialized functions. Such reactions on polymers are usually called grafting. Functional groups (E) which have been grafted onto polymers cover an exceedingly wide range of possibilities. They can allow catalytically active groups, fluorescent groups, hydrophobic or hydrophilic modifiers, etc. Another important use of the 1-N site is its potential for crosslinking. A bifunctional electrophile such as 1,6-dibromohexane or bifunctional epoxides commonly used for urethane crosslinking, could be applied to this system. This method could be applied to monomers prior to polymerization or to pendant groups with the polymer after polymerization.

The monomer selected for copolymerization with the substituted imidazole ring compound, homopolymer or copolymer produced therefrom may be any monomeric compound which typically is capable of undergoing copolymerization reactions. Monomers capable of undergoing addition polymerization reactions are particularly favored. Such monomers include, but are not limited to, styrene, styrene derivatives, dienes such as isoprene, butadiene, chloroprene, cyclopentadiene, and substituted acrylate esters such as alkyl methacrylates. Among the alkyl methacrylates, methyl methacrylate is particularly preferred. Other materials which can be employed as monomers include materials such as acrylonitrile.

Methods for forming the substituted imidazole monomer and its derivatives as well as copolymers produced therewith will now be described.

There are two general routes to prepare the 4,5-dicyanoimidazoles from diaminomaleonitrile (DAMN). It is possible to start from an electrophile which is an acid or a masked acid such as orthoformate. This method was originally described by Woodward in U.S. Pat. No. 2,534,331 (1950), which is incorporated herein by reference in its entirety. Alternately, one can start from a mono Schiff base and carry out oxidative ring closure. This is similar to a method as described in U.S. Pat. No. 4,220,466 (1980) to Patel, which is incorporated by reference in its entirety.

The methodology begins by reaction of DAMN with acrolein or simple substituted acroleins such as meth acrolein and crotonaldehyde. The oxidation of these acrylic monoanils leads directly to 2-vinyl-4,5-dicyanoimidazoles. The parent monomer of this family is 1-H-2-vinyl-4,5-dicyanoimidazole and has the empirical formula $C_7H_4N_4$. It contains approximately 39% nitrogen by weight. The initial materials, acrodamn and substituted variations such as crotodamn and methacrodamn, are prepared by processes given in U.S. Pat. No. 5,712,408 to Rasmussen et al. incorporated herein by reference in its entirety.

Figure 2:
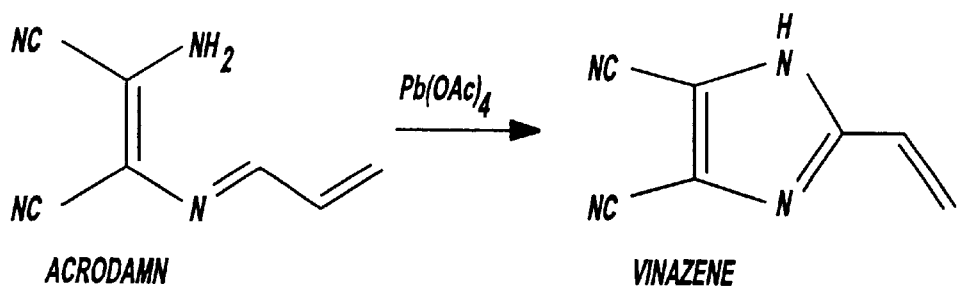
FIG. 2 is an illustration of a basic reaction for preparing 2-vinyl-4,5-dicyanoimidazole.

The methodology makes use of unsaturated monoanils of DAMN as starting materials for the preparation of 2-vinyl-4,5-dicyanoimidazoles. The monoanils can be oxidatively ring closed using oxidants such as lead tetraacetate to afford vinyl imidazoles. For example the acrodamn compound is oxidized to 1-H-2-vinyl-4,5-dicyanoimidazole as shown in FIG. 2.

Synthesis of 2-Vinyl-4,5-Dicyanoimidazole

N-(cis-1,2-dicyano-2-amino vinyl)-2-propenimine) (hereafter Acrodamn) was synthesized according to the method outlined in U.S. Pat. No. 5,712,408 to Rasmussen et al.

Acrodamn thus produced (7.000 g) was dissolved in 150 ml distilled acetonitrile, yielding an orange solution. A solution of 22.5 g of lead (IV) tetra acetate and 300 ml of distilled acetonitrile was placed in a room temperature water bath. The acrodamn/acetonitrile solution was poured, in one portion, into the lead (IV) tetra-acetate solution. The colorless lead solution immediately darkened to an orange-red solution and a white, voluminous precipitate appeared. The solution was allowed to stir for 10 minutes, and then filtered. The resulting precipitate was washed via filtration until no more color was liberated in the filtrate. The filtrate was then distilled by rotary vacuum evaporation technique (rotovapped) and stripped with a vacuum pump. To the resulting residue, 400 ml of ether was added and allowed to stir overnight. The ether solution was filtered and rotovapped to yield 5.63 grams of 2-vinyl-4,5-dicyanoimidazole (82%) as a reddish solid. The crude product was purified by dissolving in a minimum of ethyl acetate. The ethyl acetate was poured into ether, the resulting precipitate was filtered and the filtrate evaporated. Detailed characterization data for the new compound are as follows:

Mp 168–170° C. (Dec.), IR 3310 (—NH), 2241 (—CN), 1640, 1619, 1510, 1431, 1405, 1300, 1069, 1003 cm–1; NMR (DMSO-d) σ 5.2 (dd, J=10.95, 2.06 Hz, 1H), 5.9 (dd, J=17.61, 2.06 Hz) 6.5 (dd, J=17.61, 10.95 Hz, 1H).

Figure 3:
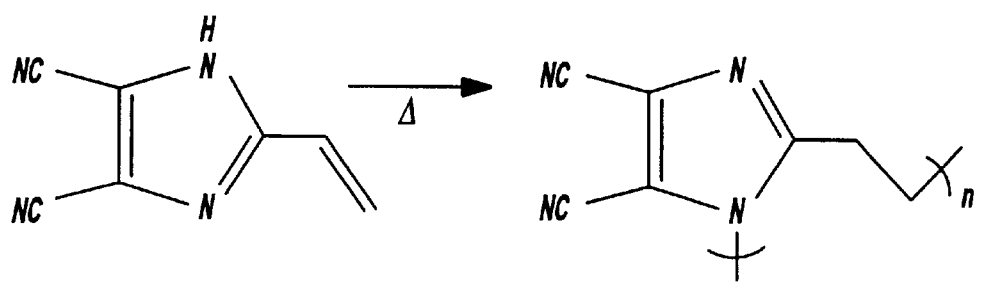
FIG. 3 shows the monomer of FIG. 2 under thermolysis to achieve Michael-type addition polymerization to form the polymer with the imidazole "in-chain", the linkage is achieved through the 7 carbon and 1 nitrogen.
Figure 4:
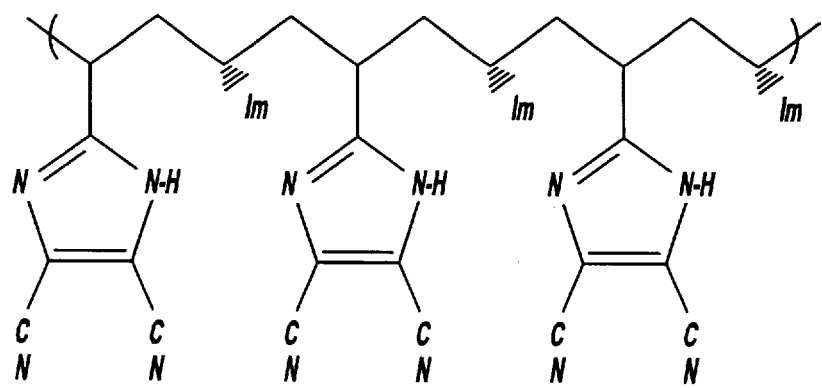
FIG. 4 shows the monomer of FIG. 2 after free radical addition polymerization. Here, alternate imidazole rings are abbreviated as "Im" for clarity. The rings are pendant to a back bone by linkage at the 2 position carbon.

This parent monomer polymerizes in two ways. Under thermolysis, it undergoes Michael-type addition polymerization to form the polymer with the imidazole "in chain" as shown in FIG. 3. If, however, the same monomer is treated with free radical initiator, such as benzoyl peroxide or AIBN a vinylicly derived free radical polymerization is induced in which the cyanoimidazole rings are pendant from the polymethylene backbone, as shown in FIG. 4.

Figure 5:
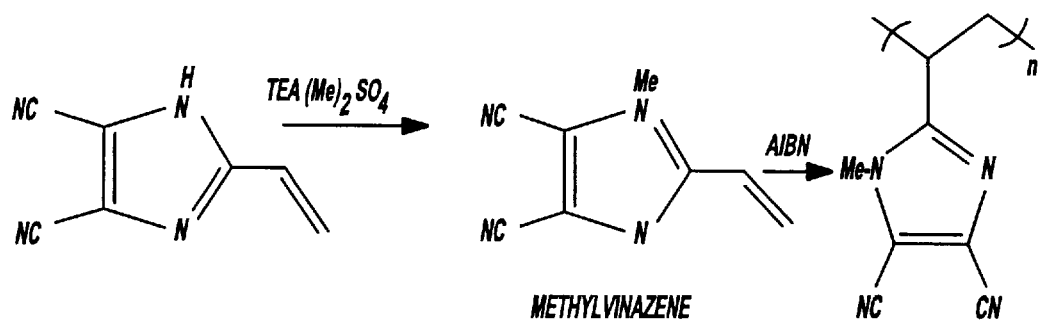
FIG. 5 shows the monomer of FIG. 2 alkylated to form methyl-VINAZENE™(1-methyl-2-vinyl-4,5-dicyanoimidazole) the 1-substituted monomer undergoes vinylic polymerization by AIBN initiator.

The present invention makes use of the fact that the VINAZENE™ monomer can be alkylated or otherwise protected without inducing polymerization. For example, the monomer can be methylated as shown in FIG. 5. If the initiator azobisisobutyronitrile (AIBN) is introduced, homopolymerizarion will proceed. However if left uninitiated, the alkylated VINAZENE™ monomer can be employed in subsequent copolymerization processes with various monomers capable of undergoing addition polymerization.

Another aspect of the invention concerns the fact that the monomer described above, can be alkylated or otherwise protected without inducing polymerization. Thus for example, it can be methylated as in the method outlined below. The resulting 1-protected monomer, methyl-VINAZENE™, also undergoes vinylic polymerization, for example by the initiator AIBN as in FIG. 5. In this example, a polymer of viscosity average molecular weight 140,000 was prepared at 65° C. in acetonitrile.

This same monomer can be polymerized by anionic initiation, for example, by the use of fluorenyl lithium. This initiator, which is known to initiate acrylonitrile, but not styrene, places the monomer among those polymerized by mild anionic methods. This placement makes it possible to readily form copolymers and block copolymers of this and related monomers, with styrene, acrylonitrile, and other large volume monomers in the manner to be discussed subsequently. Such monomers are initiated under similar conditions.

Figure 6:
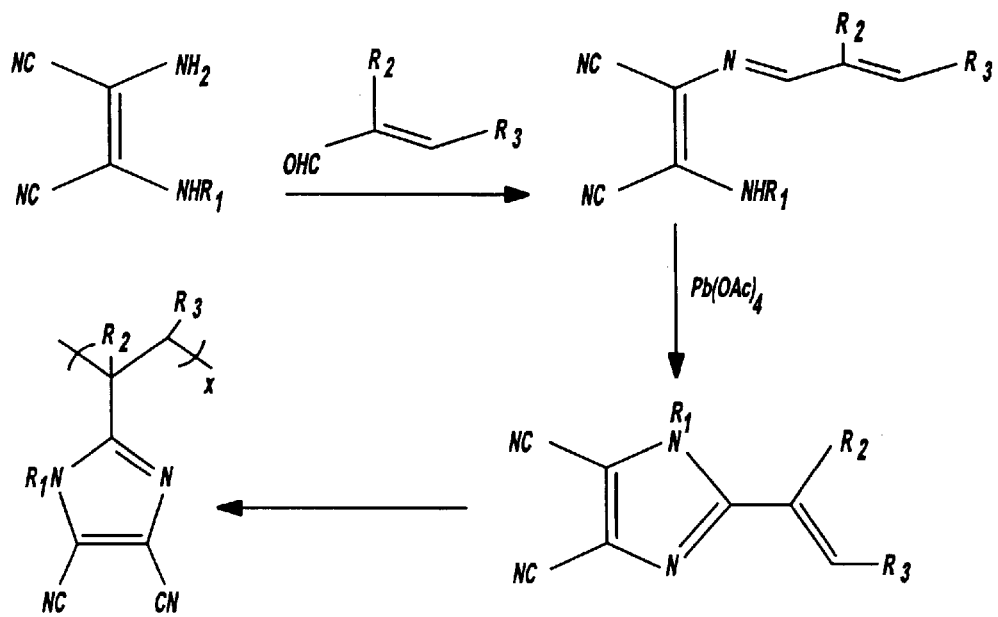
FIG. 6 shows that the varying substitutes R1, R2 and R3 are usable to form starting materials.

The monomer(s) are easily modified by using various substituents (R1), at the 1-nitrogen as described above. However, by varying the starting materials, the substituents R2, and R3 an also be varied, as per FIG. 6.

As described above, there were prepared Schiff base derivatives of DAMN using different aldehydes, for example, methacrodamn, R2=methyl, R3=H; crotodamn, R2=H, R3=methyl. Schiff bases derived from N-ethylDAMN (R1=ethyl) can also be oxidized by the methods described above to afford the corresponding cyanoimidazole derivatives. Thus, for example, N-ethylmethacrodamn is oxidized to 1-ethyl-2-[1-methyl vinyl]-4,5-dicyanoimidazole, as per FIG. 7.

The new polymers are useful in applications and end uses which call for higher thermal and oxidative stability than conventional vinylic polymers. The nitrogen content of the parent monomer, 1-H-2-vinyl-4,5-dicyanoimidazole, and its polymers is, for example, 39% by weight. This high nitrogen content, along with the intrinsic stability of the imidazole ring system, gives the polymers potential for providing inhibition of flammability, higher softening temperatures, and greater char yields than conventional materials. A summary of the advantages found in pursuing applications for these new polymers are described below.

There is a moderate cost structure. Synthesis of monomers occurs in one or two steps from starting materials that are nearly commodities. Although polymers directly derived from acrolein are uncommon, this material has a current world production estimated at 125,000 tons per year. DAMN is a stable solid, marketed by Nippon Soda Co. at moderate prices. The monomers polymerize very readily by thermal or chemical initiation at very moderate temperatures to afford polymers. These polymers have high thermal stability and they decompose with low gas evolution. Once the cyclization to imidazole takes place, the heteroaromatic stability long associated with this ring system in polymer chemistry provides very robust materials. The stoichiometric composition of the materials, with their very high nitrogen and low hydrogen content, suggests their use as flame retardants, protective coatings, and in specialty materials which demand high oxidation resistance.

The monomers or the polymers are easily modified. The family of derivatives appears to be limited only by the range of electrophiles which will readily attach to the 1-N. Since cyanoimidazole anion is a good leaving group, the 1,3 sites can function together in a catalytic mode for the transfer of attached groups. Grafting reactions should also be very facile. The cyano groups can be hydrolyzed before or after polymerization to afford amides or carboxylic acid. This may prove to be a highly economical route to cation exchange resins or metal ion sequestering polymers.

Alkylated VINAZENE™ compounds can be produced in the manner outlined below.

Synthesis of 1-Methyl-2-vinyl-4,5-dicyanoimidazole (1-Methyl-VINAZENE™)

Generally speaking 1-methyl-2-vinyl-4,5-dicyanoimidazole is produced by the reaction of VINAZENE™ with triethylamine in the presence of an organic sulfate such as dimethyl sulfate as outlined in FIG. 5. Specific synthesis of 1-methyl-VINAZENE™ is outlined as follows. It should be understood that Schiff base derivatives of DAMN using different aldehydes such as methacrodamn can be employed.

To a solution of 0.602 g (4.17 mmol) of 2-vinyl-4,5-dicyanoimidazole in distilled THF (15 mL) at 0° C. blanketed under nitrogen, 0.44 mL (4.6 mmol) of dimethyl sulfate and 0.60 mL (4.30 mmol) triethylamiine was added slowly via syringe while stirring. The reaction solution was allowed to come to room temperature and was stirred for 15 hours.

The reaction solution was concentrated down under a stream of nitrogen and was dissolved in 10 mL $CH_2Cl_2$. This solution was washed twice with a 10% solution of NaOH and twice with a saturated solution of NaCl. The $CH_2Cl_2$ was stripped off leaving a brown oil. This oil was dissolved in approximately 1 mL of THF and precipitated out in hexane.

The precipitate was vacuum filtered and dried to yield 0.345 g (52.4 yield %) of a light brown, fluffy powder. This powder was dissolved in 10 mL of ether and vacuum filtered to remove undissolved particles. 20 mL of hexane was added to the ether solution, and the solution was cooled to 0° C. White needle-shaped crystals were formed and vacuum filtered.

Mp 96–98° C.; IR 2237 (—CN), 1492, 1464, 1420, 1378, 1328, 986, 948, and 765 cm–1; NMR (DMSO-$d_6$) 3.8(s, 3H, —$CH_3$), 5.8 (dd J=10,89, 1.09 Hz, 1H), 6.3(dd, J=17.35, 1.09 Hz, 1H), 6.9 (dd, J=17.35, 10.89, 1H).

Synthesis of 1-Ethyl-2-vinyl-4,5-dicyanoimidazole (1-Ethyl-VINAZENE™)

A 1-ethyl derivative of VINAZENE™ can be prepared by the reaction of VINAZENE™ with triethylamine and diethyl sulfate in a THF solution. Specific synthesis of 1-ethyl-VINAZENE™ is outlined as follows.

Figure 7:
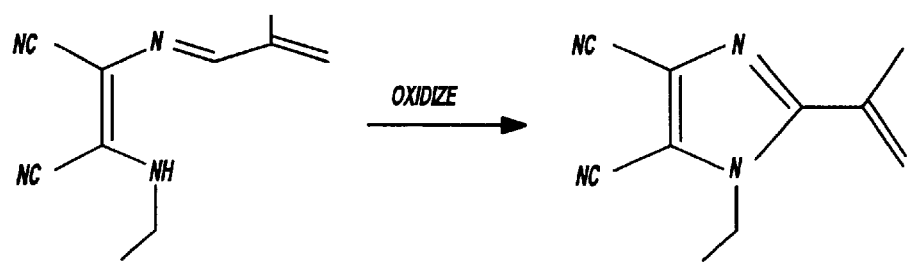
FIG. 7 shows an example of forming a cyclic dicyanoimidazole compound using a Schiff base derived from N-ethyl DAMN (N-ethyl diaminomaleonitrile)

It is to be understood that it is also possible to employ Schiff base derivatives of DAMN using different aldehydes such as methacrodamn. Schiff bases derived from N-ethyl DAMN can also be oxidized by the methods outlined to afford corresponding cyanoimidazole derivatives. As shown in FIG. 7, N-ethylmethacrodamn is oxidized to 1-ethyl-2-[1-methyl vinyl-4,5-dicyanoimidazole].

A flask equipped with an electric stir bar was charged with 6.26 g of 2-vinyl-4,5-dicyanoimidazole. To this, 75 ml of distilled THF and 6.1 ml of triethylamine were added with stirring. After 5 minutes stirring, 5.7 ml of diethyl sulphate was added. This mixture was allowed to stir for 2 days. Analysis by TLC (50/50 hexane/ethyl acetate, UV visualization) showed the reaction was complete (starting material rf 0.3, product rf 0.6). The THF solution was rotovapped and the residue dissolved in ethyl acetate. The ethyl acetate was washed with 10% aqueous sodium hydroxide. The combined aqueous layers were back extracted with methylene chloride. The combined organic layers were dried with magnesium sulphate and rotovapped to dryness. The crude residue was triturated with ether. The ether extracts were rotovapped and the residue recrystalized with ether/hexanes to yield 3.124 g of product, mp 66–70° C. as yellow needles. A second crop yielded 1.72 g for a combined yield of 65%.

H NMR: 6.95, 1H (dd J=17.04, 10.99 Hz); 6.36, 1H (dd J=17.04, 1.38 Hz); 5.81, 1H (dd J=10.99, 1.38 Hz); 4.28, 2H(q J=7.14 Hz); 1.33, 3H (t J=7.14 Hz).

Applications and Advantages

In polymer chemistry, there are relatively few families of useful vinylic monomers. Since the steric and electronic properties of a good monomer are quite well known, and a terminal vinyl group can only have two functionalities, one might be justified in assuming that all simply prepared vinylic monomers have already been discovered. The present invention shows that this is not the case, based on a new family of monomers based on 2-vinyl-4,5-dicyanoimidazole. The parent monomer is prepared by oxidation of acrodamn, which is the mono Schiff base of diaminomaleonitrile (DAMN) and acrolein. Since DAMN is the tetramer of hydrogen cyanide and acrolein is prepared by oxidation of propene, one can prepare 2-vinyl-4,5-dicyanoimidazole and its derivatives from readily available, moderately priced, starting materials. Once the oxidative cyclization occurs, the highly stable imidazole ring system prevents reverse reactions. In spite of high nitrogen content, these polymers lose very little HCN or cyanogen by thermal processes.

The dicyanoimidazole ring system is in conjugation with the 2-vinyl group, and this heterocycle has electron withdrawing effects similar to, but slightly weaker than, a simple cyano substituent. Thus, 2-vinyl-4,5-dicyanoimidazole behaves sterically like styrene and electronically like acrylonitrile or acrylic esters. The monomers polymerize very readily by free radical, or if substituted at 1-N, by anionic initiation to produce high molecular weight polymers. Unlike styrene, for which the vinylic group deactivates the ring, 2-vinyl-4,5-dicyanoimidazole is easily substituted at the 1-nitrogen by electrophiles before or after polymerization. Thus, an enormous variety of structural changes are feasible. In addition to the great flexibility offered by substitution at the 1-nitrogen, the nitriles of 4,5-dicyanoimidazole can also easily be modified to amides, carboxylic acids, or amines. Finally, in addition to polymerization of the 2-vinyl-4,5-dicyanoimidazole family of monomers, it has been found that copolymers can also be formed as discussed below.

The high nitrogein, low hydrogen stoichiometries of these materials confer some special properties. Typically, such molecules are electron acceptors and have low base strength. They are often quite oxidation resistant and flame resistant. Certain combinations can have very high thermal stability as well. Thus, high nitrogen materials are replacing halogen compounds, which have undesirable environmental effects, as flame retardants. Low hydrogen content has another benefit. Compounds with numerous cyano groups do not readily evolve HCN when H content is low. In fact, total gas evolution can be low and char yield and nitrogen retention is remarkably high, even up to 900° C. under nitrogen.

To this point, there have been only a very limited number of polymers based on HCN. Polyacrylonitrile and polyacrylates are generally derivatives of HCN, and their place among the important polymers has been established for many years. However, certain compounds, such as cyanogen and the HCN tetramer, diaminomaleonitrile (DAMN), have not led to important polymers, in spite of considerable effort. Despite this, the present invention provides several key discoveries which allow the synthesis of a new family of polymeric and copolymeric materials. The present methodology starts by the reaction of DAMN with acrolein or simple substituted acroleins such as methacrolein and crotonaldehyde. These aldehydes are readily available and like DAMN itself, can be obtained at moderate prices in large quantities. The oxidation of these acylic mono anils leads directly to 2-vinyl-4,5-dicyanoimidazoles. The parent monomer of this family, 1-H-2-vinyl-4,5-dicyanoimidazole, has the empirical formula $C_7H_4N_4$, and contains 39% nitrogen by weight.

Additionally, there are some rather subtle inductive effects which control the reactions of DAMN. For example, if one attempts to prepare monomethyl DAMN by direct alkylation, it is difficult to stop the reaction at this stage. Instead, the first methylation activates the nitrogen towards a second addition, and the two methyls activate the second nitrogen towards addition of a third methyl. Thus, the result of slow, cold addition of one equivalent of methylation agent to dilute DAMN solution is trimethyl DAMN. In sharp contrast to the methylation results, at zero degrees, with dilute acid catalyst, reaction of DAMN with acrolein forms only the mono-anil. The Schiff base formation at one nitrogen deactivates the second nitrogen towards forming the bis anil. On the other hand, the double bond, which now lies in conjugation to the DAMN end of the molecule, is highly activated.

Figure 8:
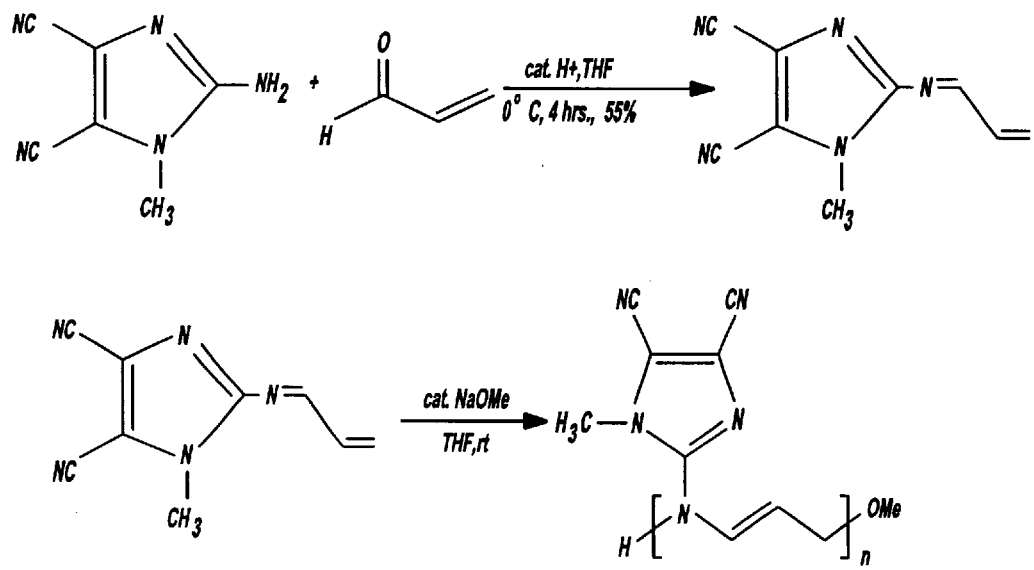
FIG. 8 is an illustration of a comparative reaction using a variation of the cyclic imidazole monomer. The Schiff base of 1-methyl-2-amino-4,5-dicyanoimidazole is formed and behaves differently from VINAZENE™.

To clarify the reactions of the Schiff base monomers, an anil was prepared from 1-methyl-2-amino-4,5-dicyanoimidazole (FIG. 8). This monomer has no nucleophilic sites which can react with the activated double bond and indeed behaves very differently from VINAZENE™ and N-methyl-VINAZENE™.

As stated earlier, there are two general routes to prepare the 4,5-dicyanomidazoles from DAMN. One can start from an electrophile, which is an acid or masked acid such as orthoformate. Alternatively, one can start from a mono Schiff base and carry out oxidative ring closure. This latter method applied to acrodamn carries out an oxidative ring closure to produce 2-vinyl-4,5-dicyanoimidazole, without inducing polymerization. The mechanism probably involves equilibrium cyclization from which aromatization proceeds by irreversible dehydrogenation. The unoptimized yields for this oxidation, which must be run carefully, are currently at 82%. The acidic imidazole (pK~5) which results can be readily alkylated in high yield without interference from the other functional groups. This reaction is a prototype for the substitution of many other electrophiles onto the 1-position of the ring.

This present application refers to these monomers by the trivial names: VINAZENE™, for the 2-vinyl-4,5-dicyanoimidazole; and methyl-VINAZENE™, etc., for its N-substituted derivatives. These monomers are fully characterized and are crystalline, air-stable, solids. However, they show a very interesting contrast in their thermal behavior. VINAZENE™ has a potential Michael nucleophile at the 1-nitrogen, while methyl-VINAZENE™ does not. The DSC of VINAZENE™ shows an exotherm following melting at 196° C., which is very similar to that of acrodamn, though not nearly as sharp. The TGA shows no weight loss in this region, and the ultimate char yield, starting from monomer, is very high.

This behavior closely mimics the behavior of the acyclic Schiff base derivatives of DAMN. One may interpret these results as evidence for a conjugate addition, step growth, type of polymerization in which the imidazole moiety is in the main chain, as shown below. However, VINAZENE™ also polymerizes in a vinylic mode by earlier radical initiation, and this polymer has a very different structure and thermal signature in the TGA, in which the char yield is lower.

On the other hand, methyl-VINAZENE™ shows no exotherm in the DSC after the melting point, and no indication of thermally induced polymerization, at least to the limit of the scan. Thus, methyl-VINAZENE™ should behave like a normal vinylic monomer carrying an electron withdrawing group. The electron withdrawing character of dicyano substitution on imidazole is here known, but it is worth noting that dicyanoimidazole is nearly nine orders of magnitude more acidic than imidazole itself, pK~14.

Figure 9:
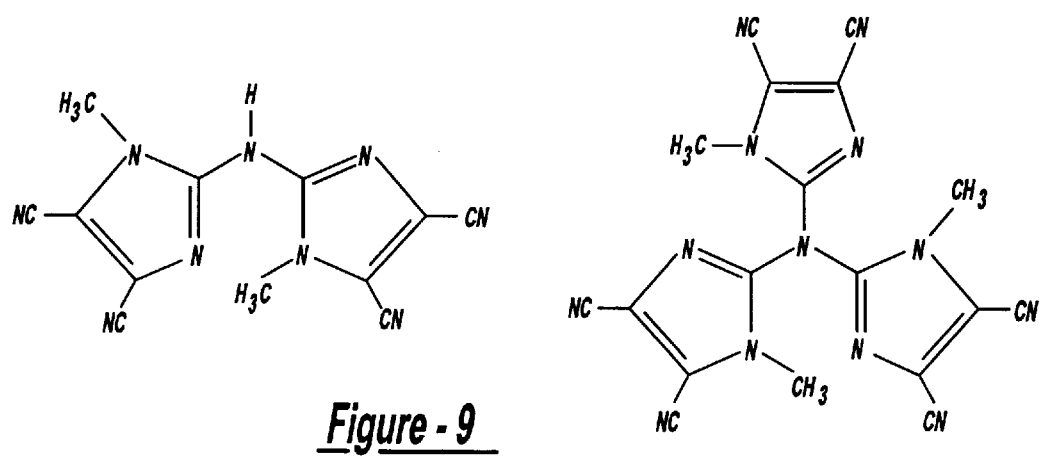
FIG. 9 shows another comparative dicyanoimidazole derivative which behaved differently from the monomers and polymers of the of the present invention.

These electron withdrawing effects have now been confirmed by several ancillary synthesis. The 1-methyl-2-fluoro-4,5-dicyanoimidzole can be used in nucleophilic aromatic substitution reactions. It reacts smoothly with most nucleophiles to allow the preparation of 2-substituted cyanoimidazoles of FIG. 9. The secondary amine has a pK~4, and the tertiary amine is nearly planar at nitrogen in its crystalline structure.

Thus, it is reasonable to place methyl-VINAZENE™ among the other vinylic monomers carrying electron withdrawing groups such as acrylonitrile, acrylic esters, or perhaps cyano substituted styrenes. Thus, the vinyl dicyanoimidazoles are a new family of monomers, prepared by a novel synthesis starting from DAMN, and have many useful properties.

The polymerization of the parent monomer, VINAZENE™, by a thermally induced Michael addition process, gives an imidazole in-chain structure. However, it also polymerizes vinylically by initiation at 110° C. with benzoyl peroxide to give viscous solutions which form free-standing films upon evaporation. This vinylic polymer has several unusual properties.

The VINAZENE™ monomer, like other dicyanoimidazoles, has a 1-H that is quite acidic, pK~5.0, and gives a pattern in its infrared spectrum which is characteristic of strong 1,3-hydrogen bonding. In the vinylic homopolymer, this hydrogen bonding will persist either in intramolecularly along the chain backbone, or intramolecularly, having the effect of locking the chains together.

In the cartoon of FIG. 4, an idealized intramolecular hydrogen bonding pattern is shown for a syndiotactic chain with alternate imidazole rings abbreviated, Im, for clarity. While this orderly array is not possible for an atactic random coil structure, the likelihood of strong intra or intermolecular 1,3-hydrogen bonding is high, since this feature is evident in crystal structures done on small cyanoimidazole molecules and in the associated infrared spectra. The polymer is, however, readily soluble in base, and one might hope that, by forming a concentrated dope of polymer in base, one could then spin the dope into acid, precipitating polymer fiber.

The 1-H polymer, with its facile reactions at the one nitrogen, can be envisaged as a site for grafting, crosslinking, or as a site for acylation transfer catalysis. In fact, imidazoles are commonly used for this latter purpose, but it would be extremely convenient to have a polymer immobilized version of such a catalyst. Appropriately grafted long chain branches could confer hydrocarbon solubility, improved processability, or opportunities for side chain functionality of almost any type. All that is needed for their synthesis is a suitable electrophilic reagent. Crosslinking reagents of different lengths could establish aspects of chain microstructure and provide for different degrees of stiffness in the products.

Since the alkyl substituted VINAZENES™ polymerize so readily, an alternative way to prepare the 1-H polymer is by a protection, polymerization, deprotection sequence analogous to the preparation of polyvinyl alcohol. This approach is useful for preparing copolymers of 1-protected monomer with other monomers. The masked form would be more compatible with styrene or acrylonitrile, for example. After copolymerization, the protecting group could be removed, or modified, to afford the desired functionality, which could be used for crosslinking, or other grafting reactions. This approach to polymer modification has seen application in polybenzimidazoles, but cyanoimidazoles are more facile leaving groups and offer a different range of substitution possibilities. Nitrile functionalities are readily hydrolyzed to carboxylic acids, so another use of this polymer is as a carboxylic acid cation exchange resin.

As noted above, the VINAZENE™ monomer can be cleanly alkylated in high yield without inducing polymerization. An initial polymerization attempt on this monomer, using AIBN in acetonitrile, led to poly(methyl-VINAZENE™), a hard, pale yellow polymer, in good yield. The structure is readily discerned from the NMR and IR spectra to be a normal polymethylene chain structure. The intrinsic viscosity in DMSO was $[\eta]$=0.6 dL/g, and using styrene values in toluene for the Mark Houwink constants, $M_v$=140,000.

Although polymerization of methyl-VINAZENE™ can be accomplished using free radical initiation, this monomer also polymerizes by anionic initiation. These experiments take advantage of the electron withdrawing power of the cyanoimidazole ring, and the initiator fluorenyl Li. Fluorene, (pK~25) is among the mildest carbanions used for inducing anionic polymerization and will initiate acrylonitrile, but not styrene. Interestingly, methyl-VINAZENE™ is initiated by Li fluorenyl in acetonitrile solution. Optimized conditions for an anionic polymerization could lead to block copolymers with styrene or acrylonitrile. Stereoregular polymerization is also a possibility, since the steric properties of the monomer are similar to styrene, and syndiotactic polystyrene is now known.

Synthesis of VINAZENE™/styrene Copolymer

In order to synthesize a VINAZENE™/styrene copolymer, VINAZENE™ or a suitable derivative such as an alkyl substituted VINAZENE™ can be admixed with styrene in the desired mole ratio and an appropriate free radical initiator can be added to the mixture. Suitable alkyl substituted VINAZENES™ which can be employed in copolymerization processes of the present invention have alkyl groups containing between one and twelve carbon atoms, with alkyl radicals selected from the group consisting of methyl, ethyl, propyl, isobutyl, benzyl, nonyl, and carbomoyl being preferred. In the preferred embodiment, the alkyl radical is present on the 1-nitrogen.

Suitable free radical initiators include but are not limited to azobisisobutyronitrile (AIBN), and benzoyl peroxide. Polymerization reaction proceeds for an interval sufficient to achieve the desired polymeric bond formation with acceleration of the reaction by suitable accelerants such as heating being permissible as required or desired. In the preferred embodiment, the reaction solution is heated to a temperature between about 60° C. and about 70° C., for an interval between about 20 minutes up to several hours.

When the reaction has proceeded to the desired degree of polymerization, the reaction can be quenched by any suitable method such as alcohol addition and cooling of the solution to form a precipitate. Suitable 1-alkyl-VINAZENES™ include but are not limited to 1-ethyl-VINAZENE™. A material such as 1-ethyl-VINAZENE™ can be synthesized by treating 4,5-dicyano-2-vinylimidazole (VINAZENE™) with diethyl sulfate, as described previously. Specific synthesis of a copolymer of styrene and 1-ethyl-VINAZENE™ is outlined as follows.

The 1-ethyl-VINAZENE™ was mixed in 10 ml reaction tubes with styrene in mole ratio proportions of 0.02, 0.04, 0.06, 0.08 and 0.20 mole styrene respectively to 1-ethyl-VINAZENE™. Azobisisobutyronitrile (AIBN) was employed as a free radical initiator. AIBN was added as an acetonitrile solution (1 mL of 0.1 g/10 ml) to each tube. Nitrogen was bubbled through each solution until degassing was complete.

Following degassing, the content of each tube was heated in an oil bath at 65° C. for an interval of 25 minutes after which the respective reactions were quenched by removal from the bath and addition of 25 ml methanol to each tube. Precipitates resulted.

The resulting precipitates were washed in ethyl ether, redissolved in tetrahydrofuran and reprecipitated with methanol. The copolymeric precipitates were vacuum dried for 24 hours and analyzed for carbon, hydrogen and nitrogen.

In Table I, the initial solution compositions are designated as "Feed" and resulting copolymer compositions as "Cop". Analytical data supports the conclusion that both monomers are incorporated into copolymers.

The five copolymer samples were dissolved in THF and analyzed by gel permeation chromatography (GPC). The results are collected in Table II.

TABLE I

| Styrene(mol) | Ethyl-vinazene(mol) | Feed Comp.(mol ratio) | Cop Comp.(mol ratio) |
| --- | --- | --- | --- |
| 0.035 | 0.0007 | 0.02 | 0.21 |
| 0.035 | 0.0014 | 0.04 | 0.31 |
| 0.035 | 0.0021 | 0.06 | 0.37 |
| 0.035 | 0.0028 | 0.08 | 0.41 |
| 0.0175 | 0.0035 | 0.20 | 0.52 |

TABLE II

| Feed. Comp.(mol ratio) | Mn | Mw | Polydispersity |
| --- | --- | --- | --- |
| 0.02 | $1.45 \times 10^5$ | $2.10 \times 10^5$ | 1.45 |
| 0.04 | $1.74 \times 10^5$ | $2.63 \times 10^5$ | 1.54 |
| 0.06 | $1.88 \times 10^5$ | $3.03 \times 10^5$ | 1.60 |
| 0.08 | $2.05 \times 10^5$ | $3.33 \times 10^5$ | 1.63 |
| 0.20 | $1.77 \times 10^5$ | $2.96 \times 10^5$ | 1.64 |

TABLE II-continued

Figure 10:
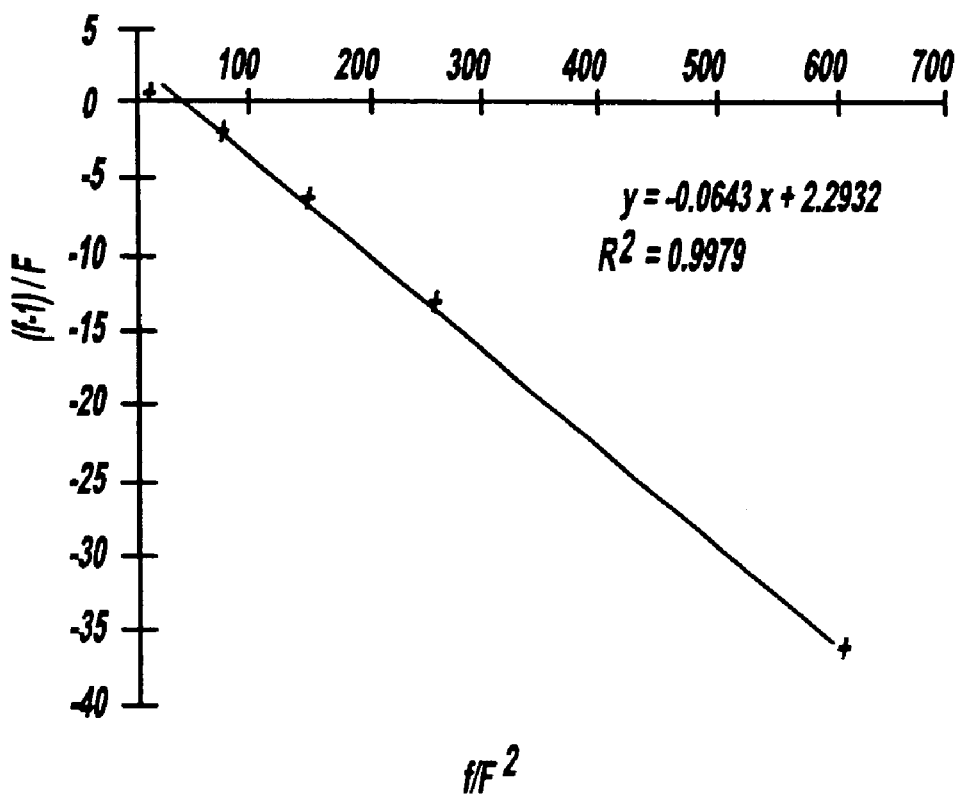
FIG. 10 is a graphic depiction of Fineman-Ross Plot for ethyl-VINAZENE™/styrene copolymerization.

The data of Table I allows the determination of the reactivity ratios for the pair of monomers ethyl-VINAZENE™/styrene. Treatment of the data by the standard method of Fineman and Ross gives the plot shown in FIG. 10 where the variable F is the composition of the feed and f is the composition of the copolymer. From this plot the values for $r_1$ and $r_2$ are 2.29 and 0.064 respectively, where $r_1$ pertains to the ratio of the rate of homopolymerization of ethyl-VINAZENE™ relative to its rate of cross propagation with styrene and $r_2$ pertains to the ratio of the rate of homopropagation of styrene relative to its rate of cross propagation with ethyl-VINAZENE™. Thus, the new monomer not only adds very rapidly itself to the active radical chain end, it can itself form a reactive chain end which reacts with either monomer.

The data of Table II gives the results of GPC measurements. From this data it can be concluded that molecular weights of the resulting material are quite high even though the polymerization reactions were quenched after relatively short intervals in order to estimate reactivity ratios. Thus, when the polymerization reactions are allowed to go to completion very high molecular weight products will result. It can also be concluded the growing radical chains are terminated largely by coupling reactions with each other rather than by chain transfer or disproportionation, given that the polydispersities are clustered around the value of 1.5.

Figure 11:
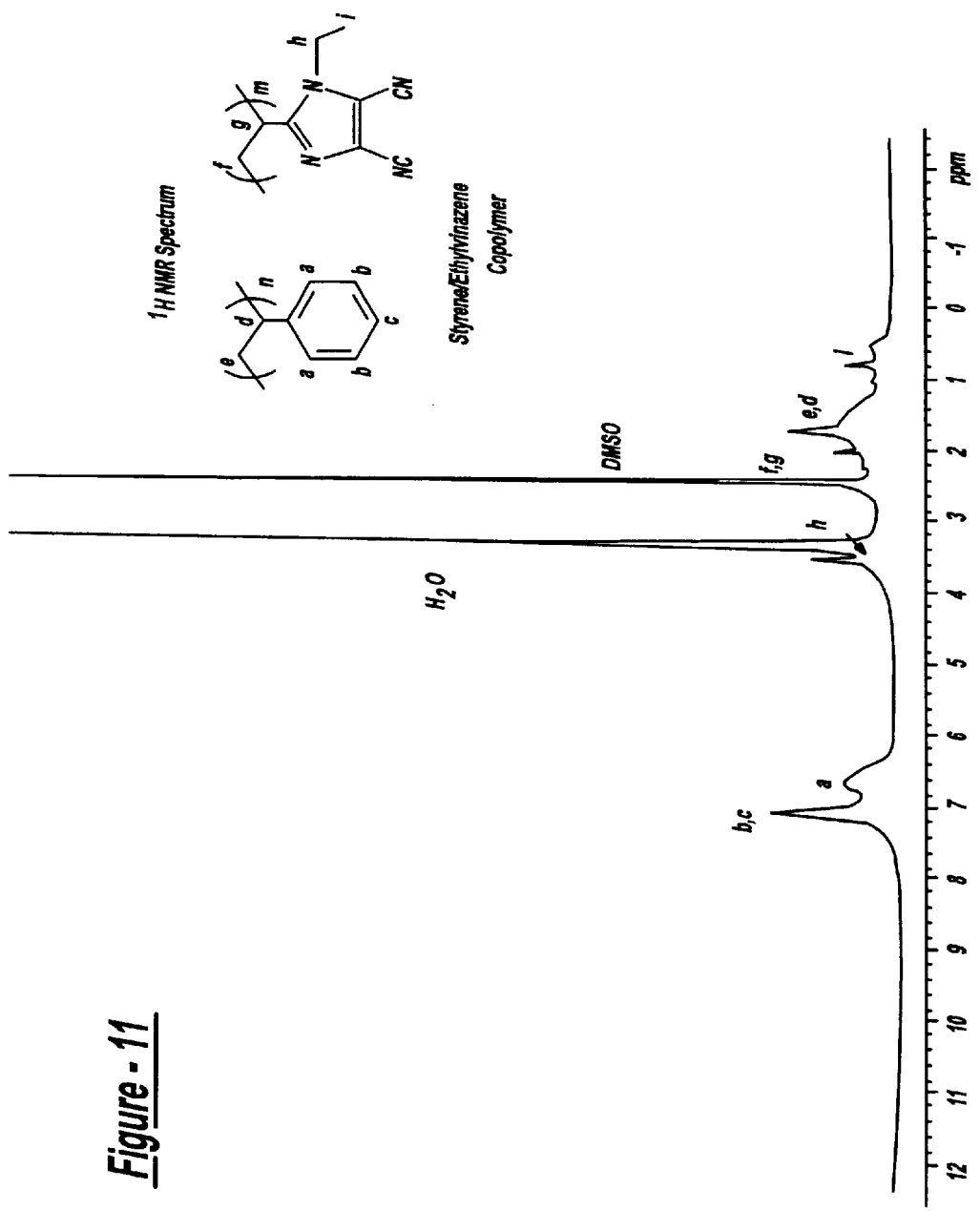
FIG. 11 is an NMR spectral analysis of the ethyl-VINAZENE™/styrene copolymer prepared according to the present invention.
Figure 12:
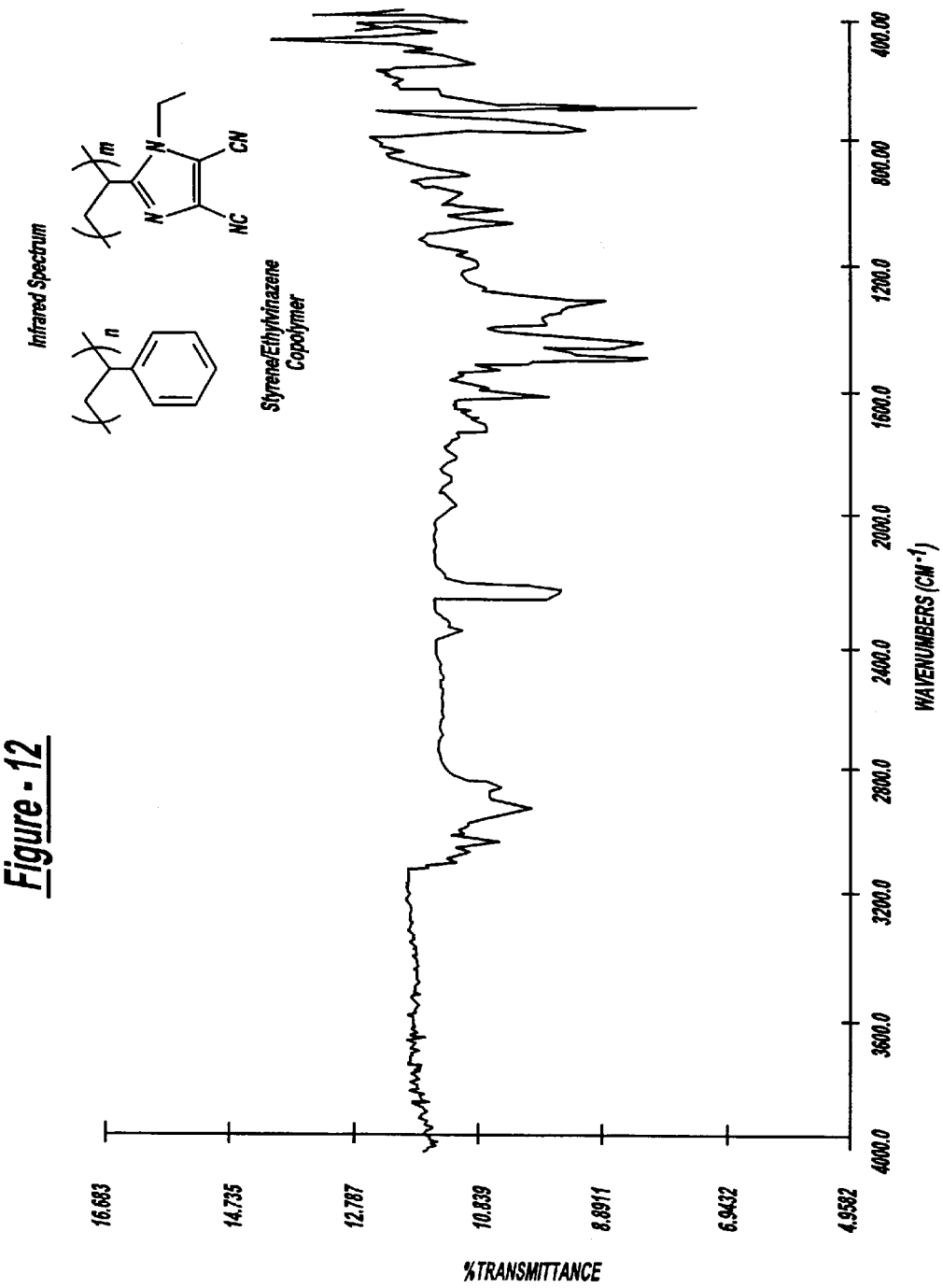
FIG. 12 is an IR spectral analysis of the ethyl-VINAZENE™/styrene copolymer prepared according to the present invention.

The ethyl-VINAZENE™/styrene copolymers were also characterized by NMR and IR spectrum analysis (FIGS. 11 and 12). The NMR analysis (see FIG. 11) was conducted in DMSO and revealed 6.9 (b,c), 7.2 (a), 1.8 (e,d), 2 (e,d). The presence of distinctive nitrile and carbonyl stretches in the IR spectrum (see FIG. 12) give evidence for the presence of copolymer.

Synthesis of Copolymers Containing VINAZENE™ and Other Monomers

Figure 13:
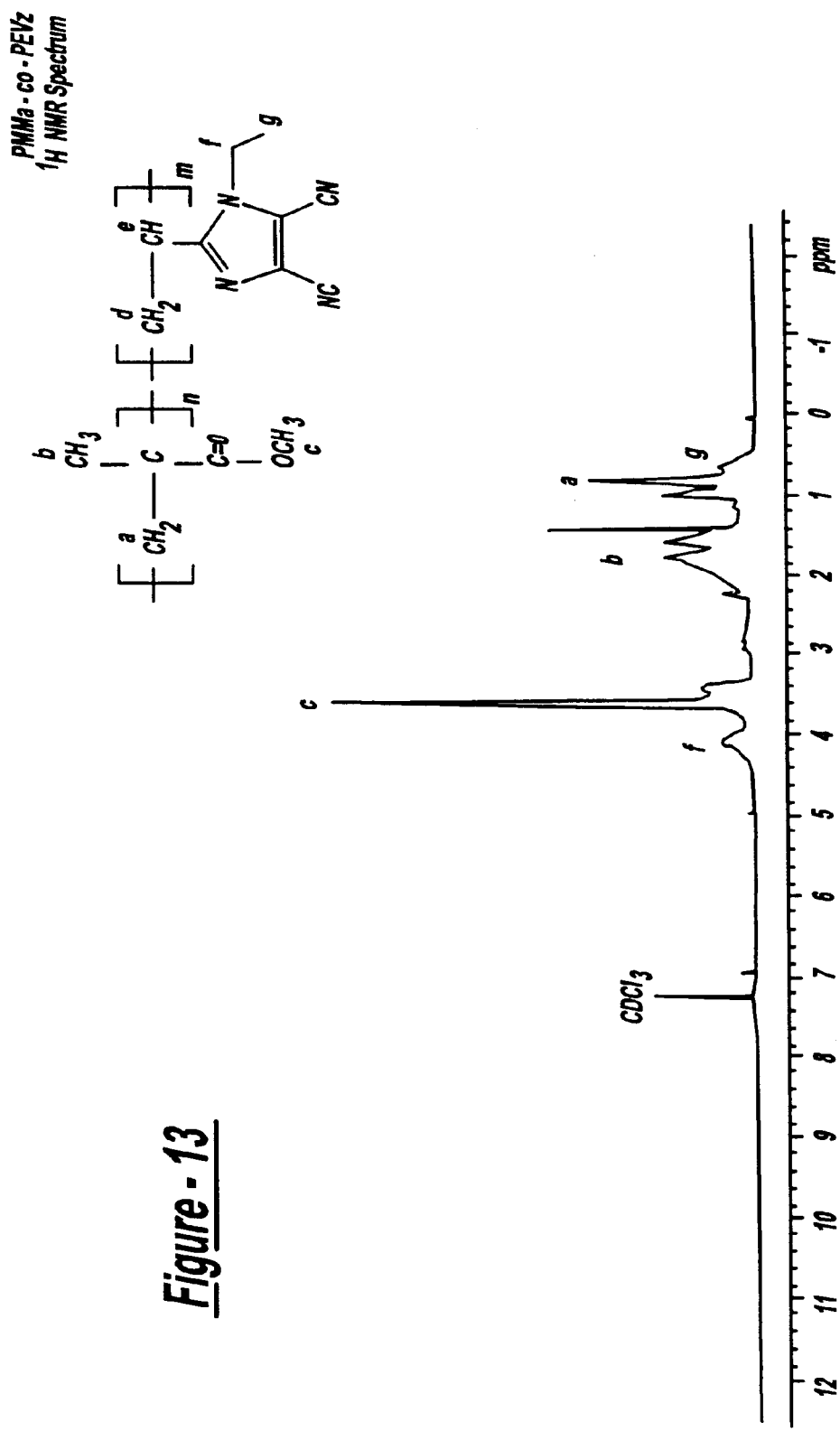
FIG. 13 is an NMR spectral analysis of the ethyl-VINAZENE™/methyl methacrylate copolymer prepared according to the present invention.
Figure 14:
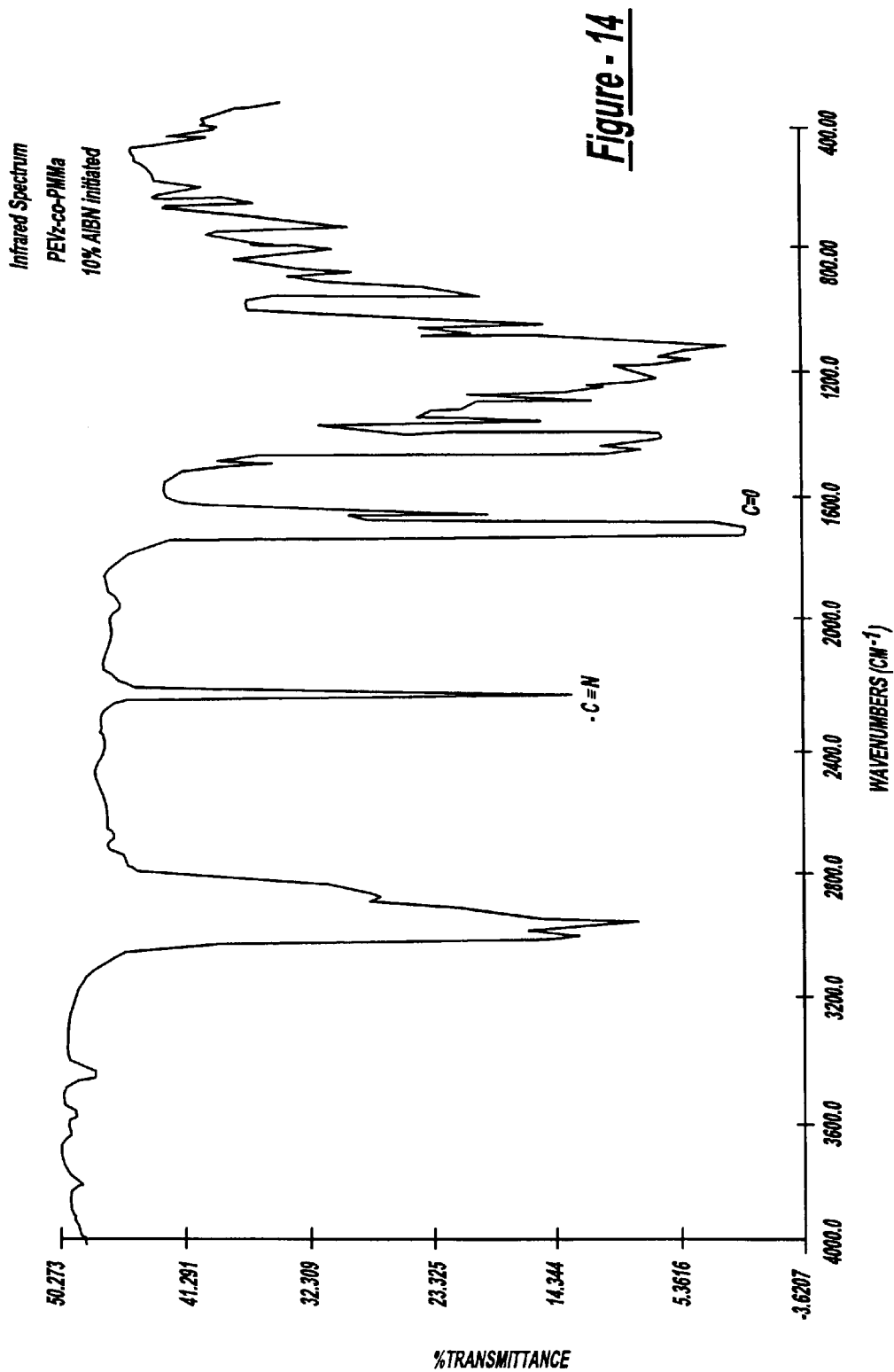
FIG. 14 is an IR spectral analysis of the ethyl-VINAZENE™/methyl methacrylate copolymer prepared according to the present invention.

VINAZENES™ and VINAZENE™ derivatives such as the alkyl-VINAZENES™ enumerated above can be copolymerized with standard monomers such as methyl methacrylate using methods such as free radical initiation. Copolymerization experiments were carried out with 1-ethyl-VINAZENE™ and the standard monomer methyl methacrylate. NMR and IR spectra analysis (FIGS. 13 and 14) give evidence of copolymerization between 1-ethyl-VINAZENE™ and methyl methacrylate as noted by distinctive nitrile and carbonyl stretches in the infrared spectrum.

Figure 15:
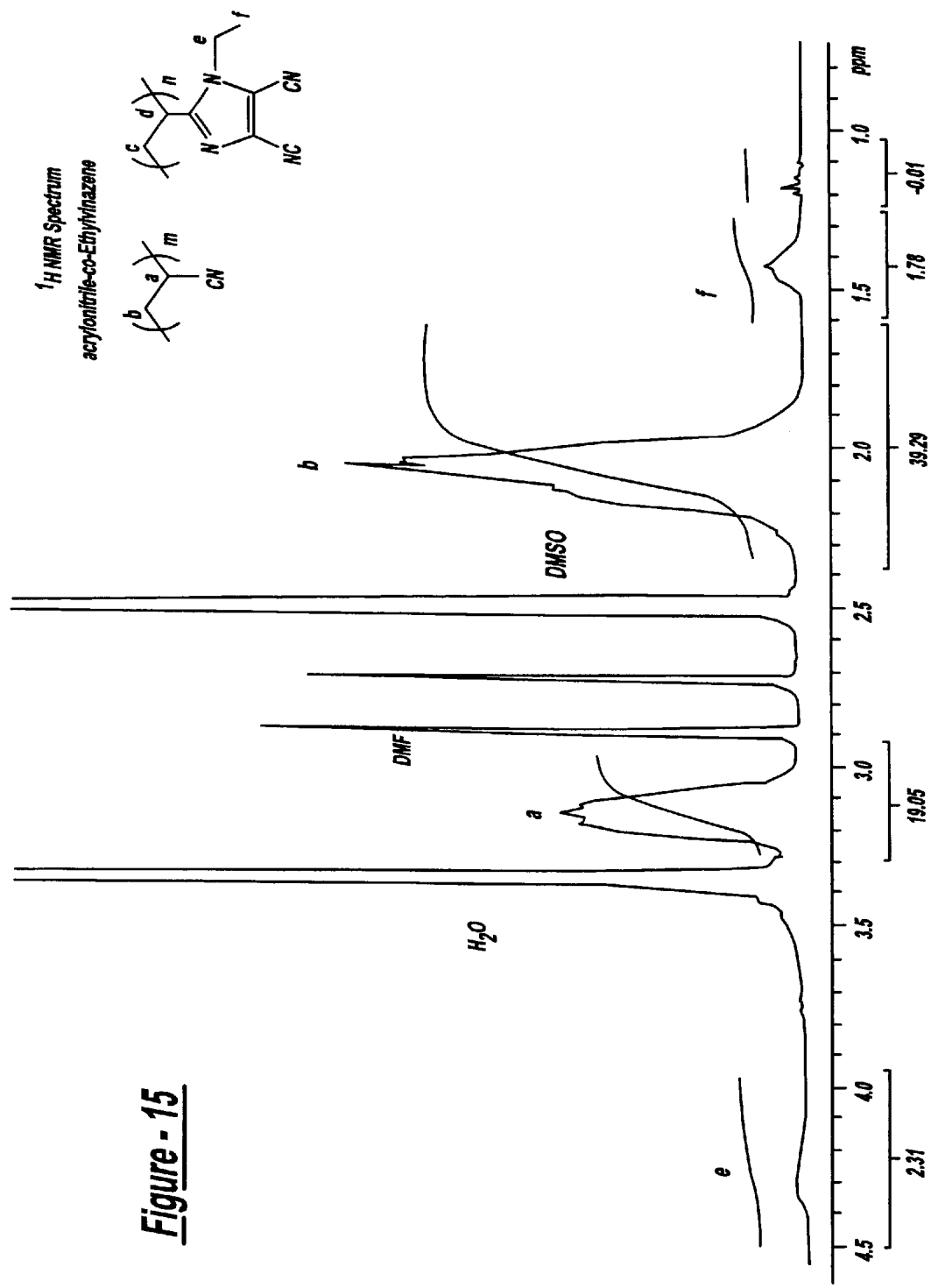
FIG. 15 is an NMR spectral analysis of the ethyl-VINAZENE™ acrylonitrile copolymer prepared according to the present invention.
Figure 16:
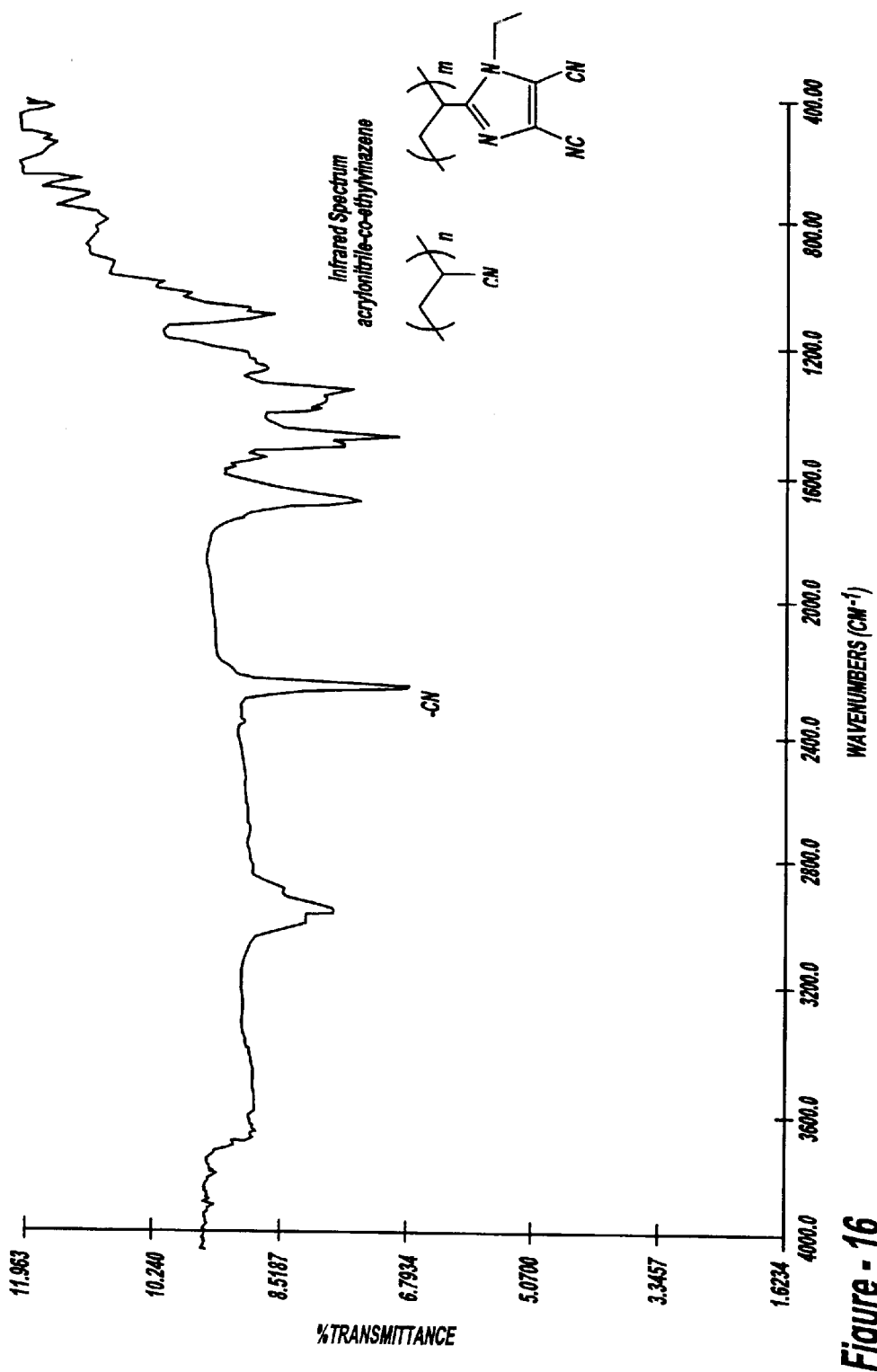
FIG. 16 is an IR spectral analysis of the ethyl-VINAZENE™/acrylonitrile copolymer prepared according to the present invention.

VINAZENES™ and VINAZENE™ derivatives such as the alkyl-VINAZENES™ enumerated above and acrylonitrile can be copolymerized in a similar manner by free radical polymerization. Copolymerization of 1-ethyl-VINAZENE™ and acrylonitrile yielded NMR and IR spectral analysis captured in FIGS. 15 and 16.

Using similar copolymerization conditions and free radical initiation methods, copolymers of alkyl-VINAZENES™ such as 1-ethyl-15-VINAZENE™ and isoprene can also be formed.

Synthesis of Terpolymers Containing Ethyl VINAZENE™

Using copolymerization conditions outlined previously and free radical initiation, terpolymers can be formed which incorporate VINAZENES™ and VINAZENES™ derivatives, i.e., alkyl-VINAZENES™ such as 1-ethyl-VINAZENE™. For example, terpolymers formed from mixtures of alkyl-VINAZENES™ such as those enumerated previously together with styrene and acrylonitrile can be produced.

Copolymerization of Alkyl-VINAZENES™ With Other Monomers Using Lewis Acid Treatment Use of Lewis acid treatment to effect copolymerization is also contemplated in the present invention. This method is effective when the comonomer pair consists of an electron poor and a relatively electron rich combination. Thus, a copolymer can be prepared from a VINAZENE™ or VINAZENE™ derivative such as an alkyl-VINAZENE™ enumerated previously using a suitable Lewis acid initiator. By way of example, 1-ethyl-VINAZENE™ and styrene can be copolymerized using a material such as $ZnCl_2$ as the initiator.

By treatment of VINAZENE™ with dimethyl sulfate, as previously described, 1-methyl-VINAZENE™ can be prepared. This derivative behaves in a manner very similar to ethyl-VINAZENE™ described above, however, if desired, the methyl can be more readily removed after polymerization by demethylation in the manner described subsequently.

Modification to the Polymerization Process to Alter Polymeric Composition

The composition of the resulting copolymers can be influenced by various means. In free radical reactions, the influence of reactivity ratios can be mediated by the addition of a stable free radical which can attach and detach reversibly from the growing chain end in the manner outlined in U.S. Pat. No. 4,581,429 to Rizzardo et al., the disclosure of which is incorporated by reference herein. In this manner, copolymerization of VINAZENES™ and VINAZENE™ derivatives such as alkyl-VINAZENES™ with various monomers can be moderated and the composition of the resulting copolymer controlled. This is particularly effective with short chain alkyl substituted VINAZENE™ such as methyl-VINAZENE™ and ethyl-VINAZENE™. Suitable mediating stable free radicals are readily known to those skilled in the art. If the respective monomers are added sequentially, for example, alkyl-VINAZENE™ followed by the standard monomer such as styrene, this living chain end method will produce block copolymers.

Stable free radical mediated reaction rates are significantly reduced compared to non-mediated rates for two monomers. Reactivity ratios are significantly different between non-mediated reactions and mediated ones. In the case of stable free radical-mediated reactions, the rate can be modified by adjusting the feed ratios of the starting materials. By varying the concentration of reactant materials, it is possible to tailor nearly "ideal" copolymerization conditions. As used herein, "ideal" is defined as similarity in reactivity ratios and monomer concentration in the feed which does not drift during the course of the reaction.

Figure 18:
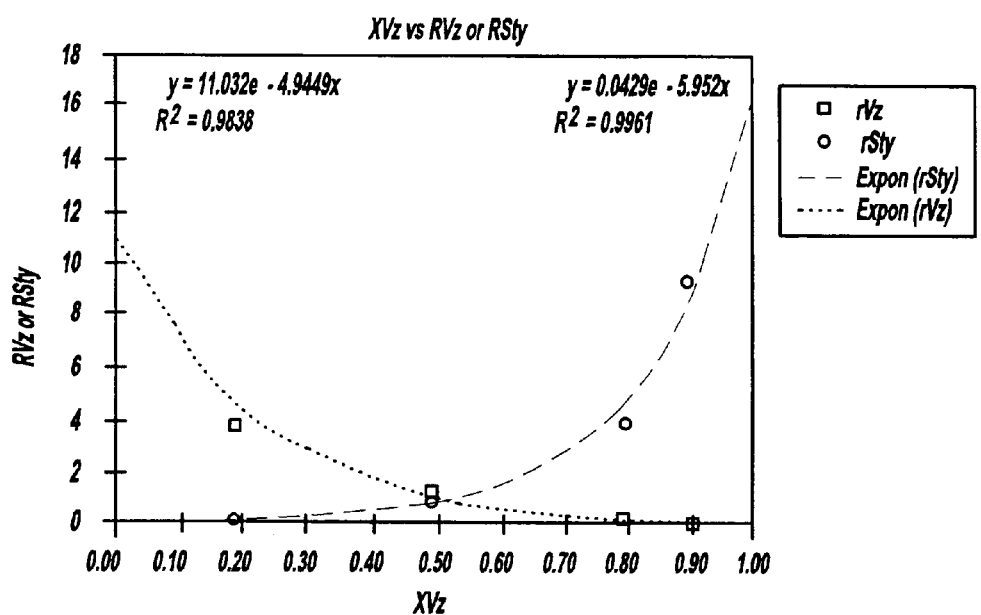
FIG. 18 is a graphic depiction of data derived from a series of kinetic runs collected from a TEMPO mediated copolymerization of methyl-VINAZENE™ and styrene expressed in the notation of the Fineman-Ross method.

As an example typical of this method, methyl-VINAZENE™, styrene and the mediating stable radical tetramethylpiperidine-N-oxide (TEMPO) were combined with AIBN. This combination was successfully accomplished both neat and in solvents such as DMF. The mixture was brought to 130° C. to activate AIBN and TEMPO. The course of the reaction was followed by observing the disappearance of each monomer as reflected in the integrated intensity of their NMR spectra, especially in the vinylic region. FIG. 18 illustrates a typical kinetics run. Addition of the monomers sequentially, for example, methyl-VINAZENE™ followed by styrene makes use of the living chain end method to produce block copolymers.

Figure 17:
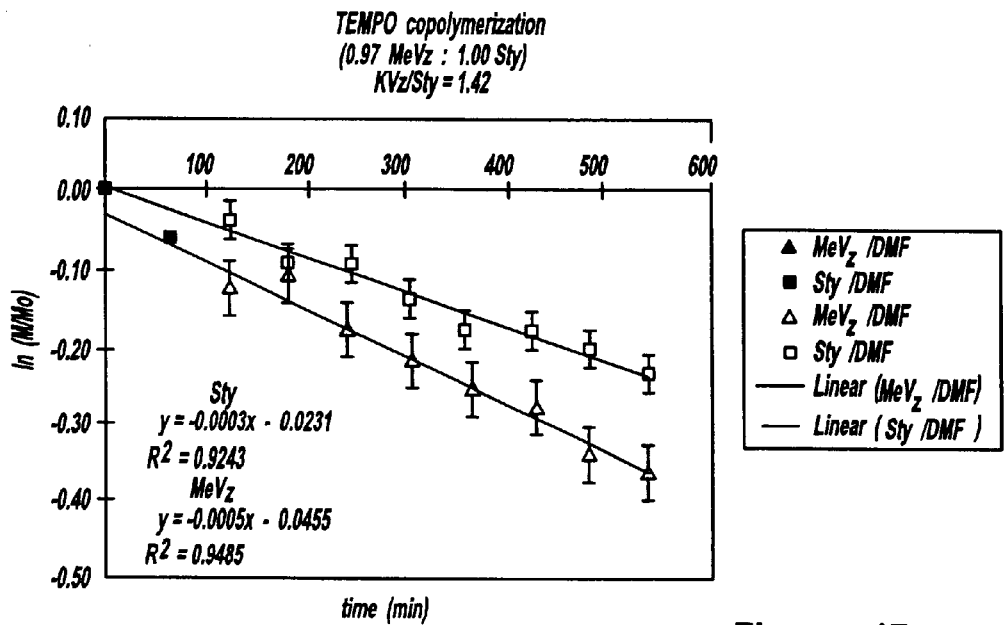
FIG. 17 is a graphic depiction of kinetics data for the copolymerization of methyl-VINAZENE™ with styrene mediated by TEMPO.

As can be seen from the data in FIG. 17, TEMPO-mediated reaction rates are significantly reduced compared to non-TEMPO-mediated rates for the two monomers with reactivity ratios being significantly different between non-mediated reactions and TEMPO-mediated ones. In the case of TEMPO-mediated reactions, adjustment of the feed ratios of the starting materials resulted in adjustment of the reaction rate. Thus variations in the concentration of reactant materials make it possible to tailor nearly "ideal" copolymerization conditions desired. This situation is illustrated in FIG. 18 where data from a series of kinetic runs leads to varying values for the reactivity ratios as a function of mole fraction of the respective monomers. The notation of the Fineman-Ross method described previously is employed.

Formation of Block Co-polymers

The electron withdrawing properties inherent in VINAZENE™ and VINAZENE™-derived monomers such as alkyl-VINAZENE™ permit anionic polymerization to occur. Block copolymerization can be achieved with the alkyl-VINAZENES™ as one monomeric component by performing anionic polymerization under living conditions using successive monomer addition. Thus, alkyl-VINAZENE™ can be initiated anionically by addition of a suitable alkaline hydride such as sodium hydride to hydrocarbon fluorene. The reaction proceeds rapidly at room temperature. The solution evidence a yellow color indicative of anionic polymerizations which persist throughout the reaction. Subsequent addition of a second monomer such as methyl methacrylate results in an alkyl-VINAZENE™/methyl methacrylate block copolymer in which block copolymerization depends on the formation of living end groups with no significant occurrence of chain transfer or termination reactions.

Similarly, block copolymerization can occur when a monomer such as styrene is initiated by the standard sodium/napthalene method in THF solution. In such a process, after polymerization was complete, the typical red color of anionic styrene polymerization persists. This indicates the presence of living end groups. While the red color persisted, an alkyl-VINAZENE™ such as 1-ethyl-VINAZENE™ was added. Solution color changed from red to violet occur. After several hours, the reaction was quenched with acid, causing the color to disappear. After precipitation of the polymer by methanol, and redissolution in a solvent such as DMF suitable polymeric material was formed.

Figure 19:
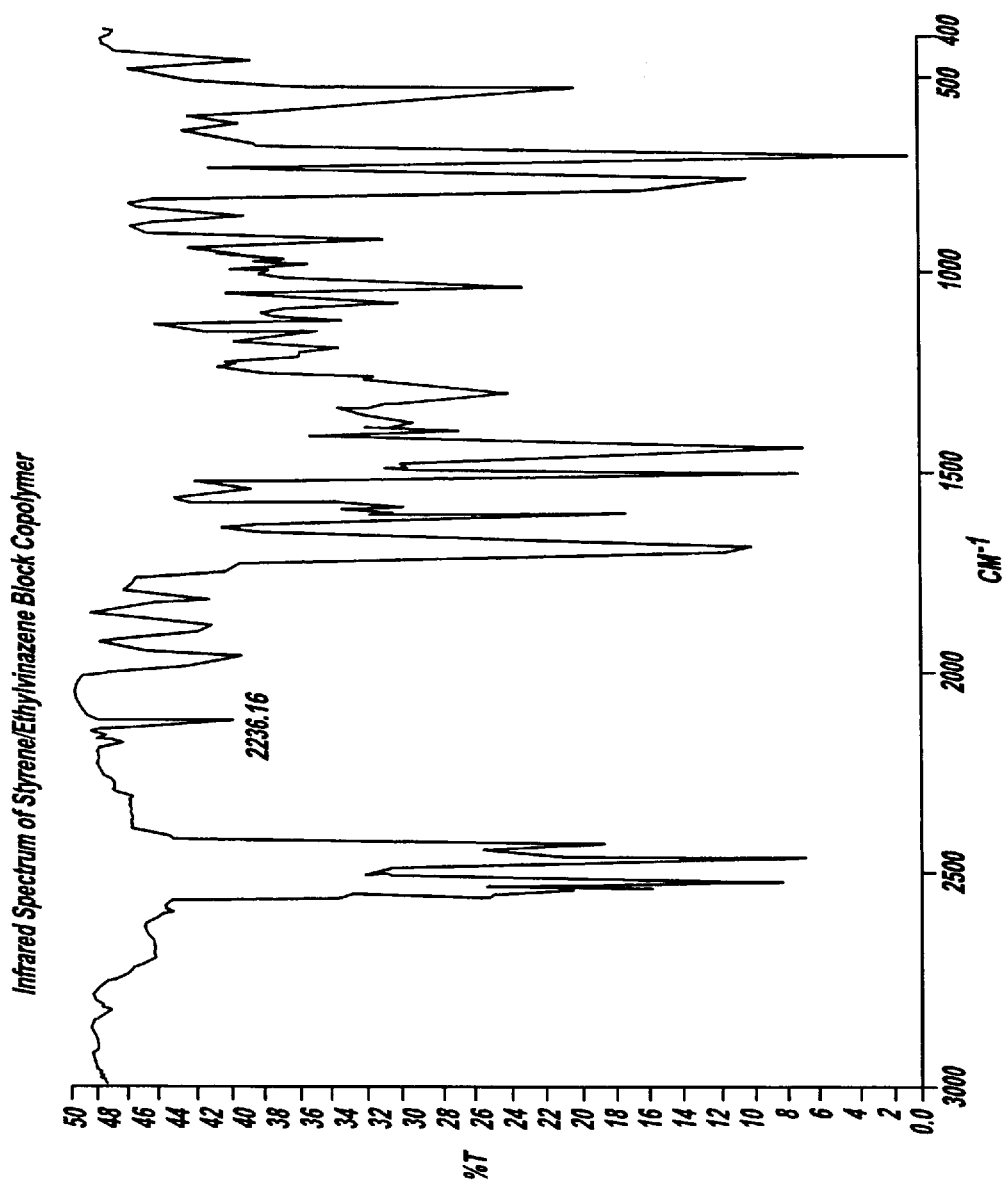
FIG. 19 is an IR spectral analysis of a styrene/ethyl-VINAZENE™ block copolymer prepared by the method of the present invention.

This procedure was performed using 1-ethyl-VINAZENE™ and styrene. The resulting polymeric material was cast as a film. The infrared spectrum of the free standing film captured in FIG. 19 shows the presence of both VINAZENE™ and styrene in the copolymer.

Properties of Resulting Copolymers

By employing alkyl-VINAZENES™ in copolymeric matrices which include standard monomers such as those previously enumerated, it is possible to advantageously modify key physical characteristics of the copolymer over the basic homopolymeric material. Particular modification includes alteration of physical properties such as glass transition temperature. Modification can occur with relatively small loading of the alkyl-VINAZENE™ into the polymeric matrix.

Copolymers of 1-ethyl-VINAZENE™ and styrene prepared by the method invention were analyzed for physical properties. The analyzed physical properties were compared against physical properties for the basic homopolymer.

Figure 20:
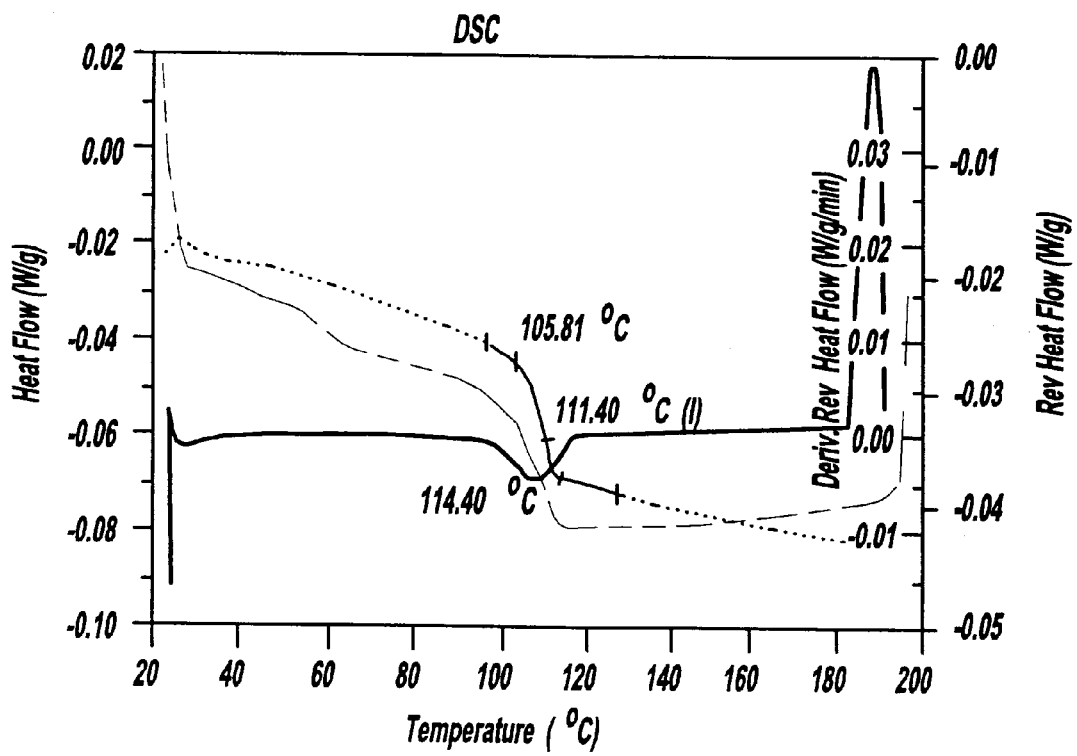
FIG. 20 is a modulated differential scanning calorigram (DSC) trace for styrene/ethyl-VINAZENE™ random copolymer prepared according to the present invention.
Figure 21:
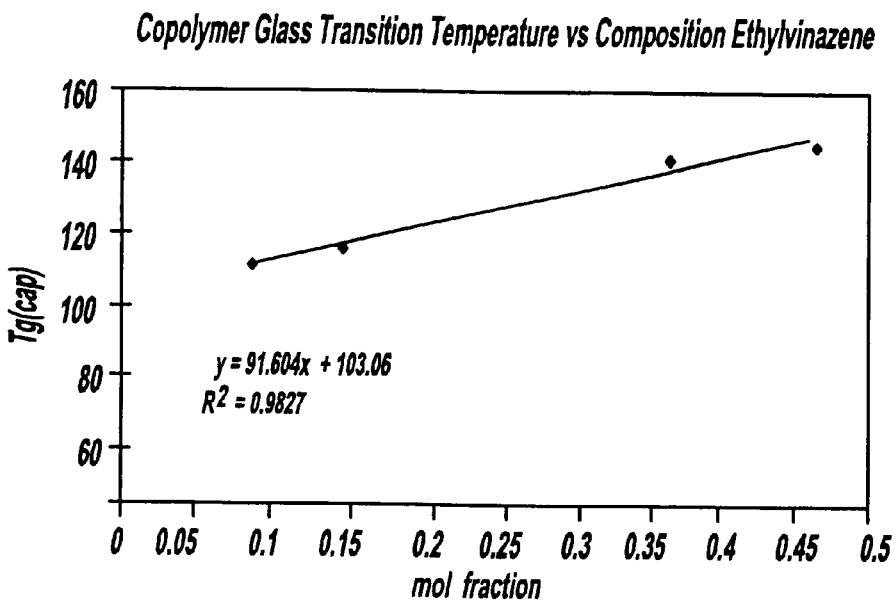
FIG. 21 is a graphic depiction of glass transition temperature versus content of ethyl-VINAZENE™ in a styrene/ethyl-VINAZENE™ copolymer prepared according to the process of the present invention.

Styrene has a glass transition temperature $T_g$ of 100° C., in some applications, a higher $T_g$ would be desirable. As indicated previously, copolymerization of an alkyl-VINAZENE™ such as 1-ethyl-VINAZENE™ with a monomer such as styrene raises the glass transition temperature smoothly as VINAZENE™ content increases. For example, at a copolymer composition of 8.8 mol% 1-ethyl-VINAZENE™, the $T_g$ of the ethyl-VINAZENE™/styrene copolymer increases from 100° C. to 111° C. A typical modulated differential scanning calorigram (DSC) trace for this copolymer is shown in FIG. 20. This trace was recorded on the second heat/cool cycle to minimize the effect of sample processing history on results. A more complete view of this relationship is shown in FIG. 21. The plot shows a linear increase in $T_g$ as a function of added ethyl-VINAZENE™.

As can be deduced from the foregoing, the useful range of an important polymer such as styrene can be extended to higher temperatures by forming copolymers with cyanoimidazole derived monomers, particularly alkyl-VINAZENES™ In addition to extending the useful temperature range of monomers such as styrene, flammability is reduced. The resulting copolymers evidence reduced tendency to burn and dripped as a result of, and in response to increased VINAZENE™ content.

The homopolymer derived from the polymerization of 4,5-dicyano-2-vinylimidazole (VINAZENE™) has hydrogen at one nitrogen. This acidic hydrogen ($pK_a$=5.5) participates in a number of reactions. It also confers solubility to the polymer in aqueous base. These desirable properties can be modified or "tuned" by combination of VINAZENE™ into copolymers. Thus, VINAZENE™ (the 1-H or parent) monomer can be employed to form copolymers. For example, the addition of AIBN to VINAZENE™ and styrene, followed by heating at 70° C. in DMF leads to a copolymer with a composition which is controlled by the feed rate and reactivity ratio previously described. The reactivity of VINAZENE™ relative to a monomer such as styrene is somewhat less than for alkylated VINAZENES™ ($r_1$=2.4, $r_2$=1.0). A convenient method of preparation is by suspension of the comonomers in vigorously stirred water. If, in addition, a small amount of divinyl benzene (1 mole%) is added, lightly cross linked beads of copolymer can be obtained which are useful as a polymer bond version of the dicyanomidazole reagent.

Alternatively, a solution polymerization can be carried out. To a test tube fitted with a stir bar, 1 ml of acetonitrile, 5 ml of styrene, 0.31 g of VINAZENE™ and 1 ml of an initiator solution containing 30 mg AIBN in 10.8 ml of acetonitrile were added. The reagents were degassed with 3 freeze-pump-thaw cycles and placed in an oil bath at 69° for 2 days. The solution became cloudy. The test tube was rinsed out with acetone and the product reduced to dryness under reduced pressure to yield a hard resin. The resin was redissolved into tetrahydrofuran and reprecipitated from hexanes. The precipitate was dried in a vacuum oven at 60° C. overnight. Pliable films could be cast of this material.

Figure 22:
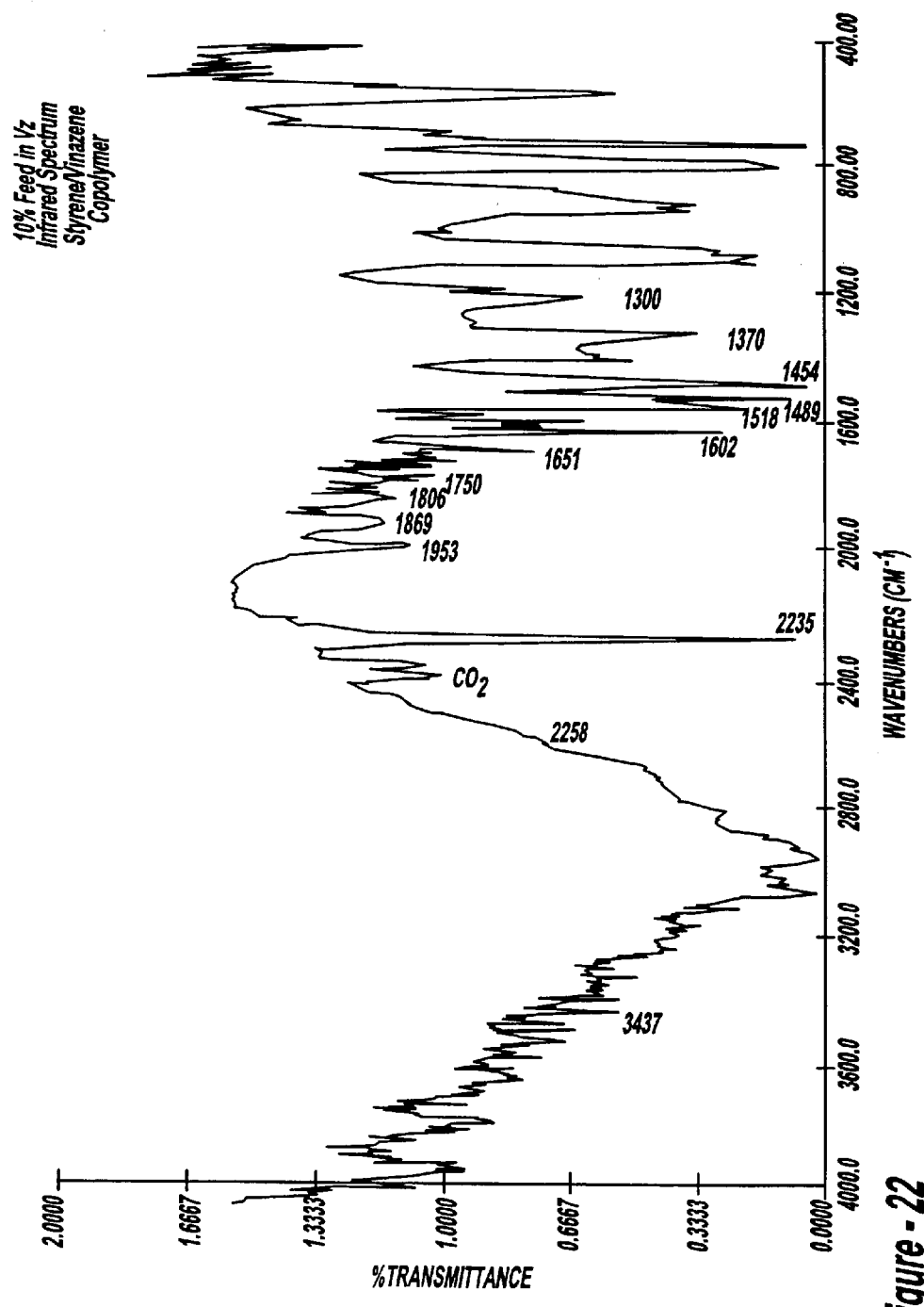
FIG. 22 is an IR spectral analysis of the VINAZENE™/styrene copolymer prepared according to the present invention at 10% feed.
Figure 23:
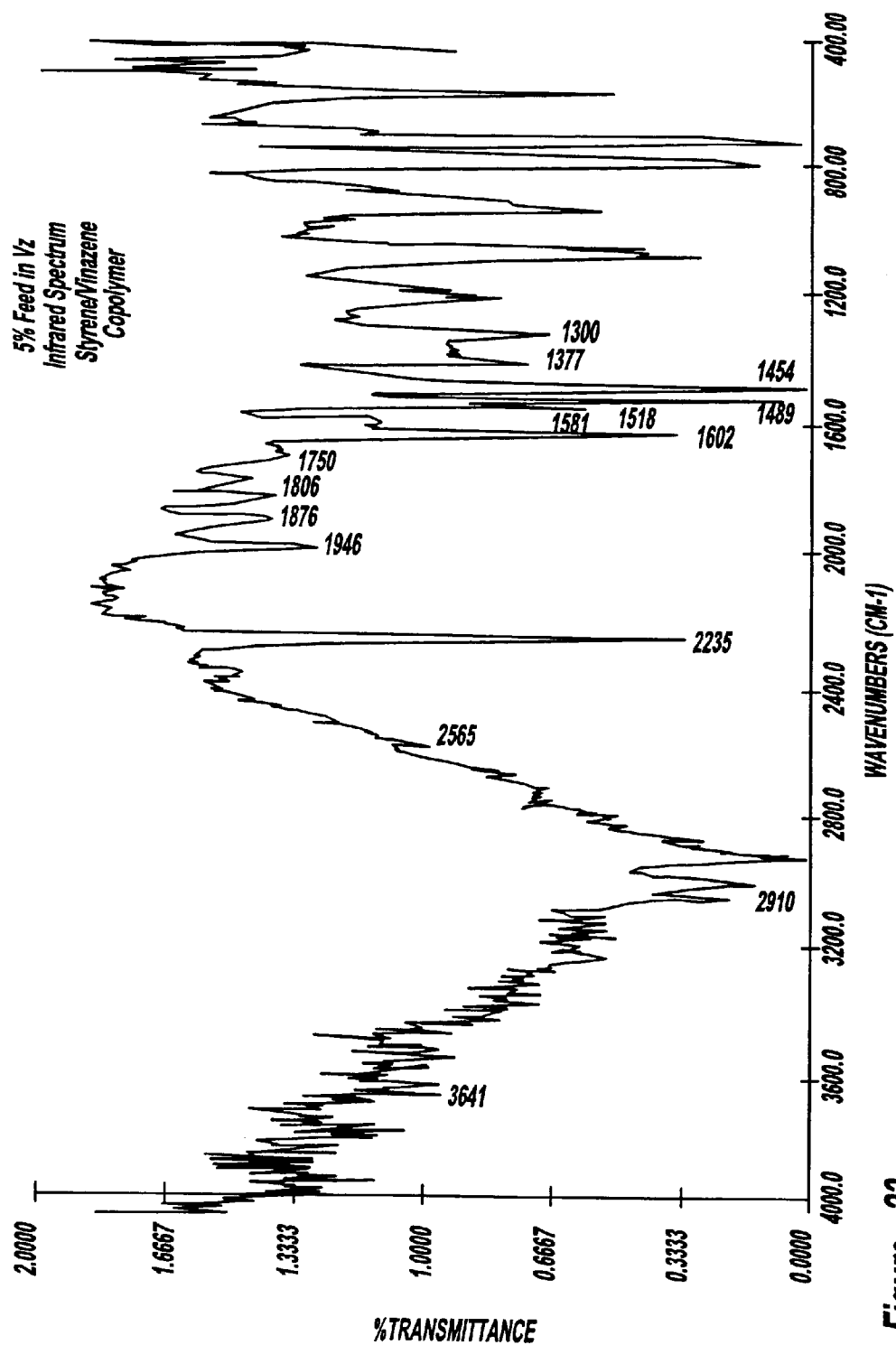
FIG. 23 is an IR spectral analysis of the VINAZENE™/styrene copolymer prepared according to the present invention at 5% feed.
Figure 24:
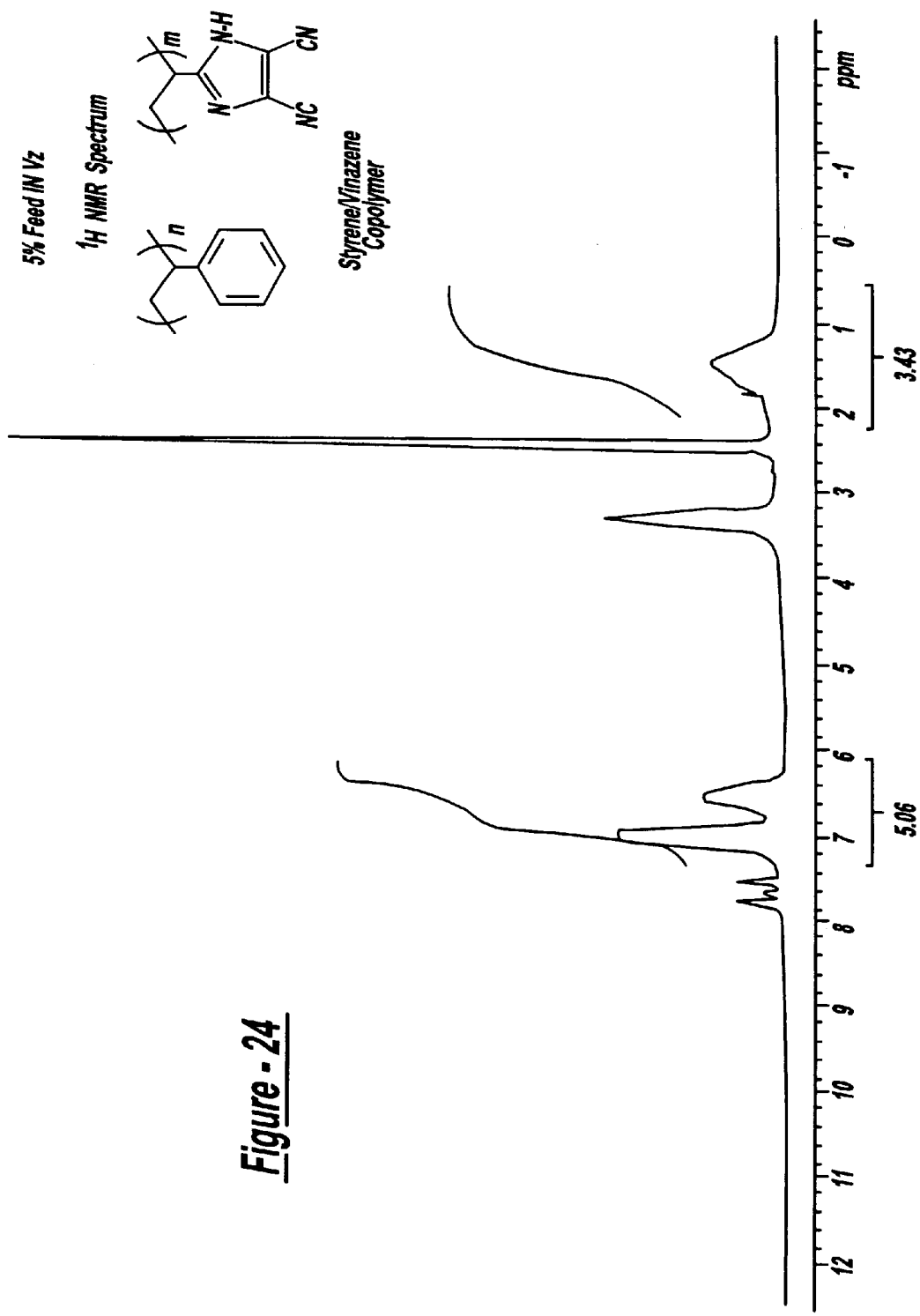
FIG. 24 is an NMR spectral analysis of the VINAZENE™/styrene copolymer prepared according to the present invention at 5% feed.

Relevant infrared spectral data are collected in FIGS. 22 and 23. Relevant NMR data are collected in FIG. 24.

Figure 25:
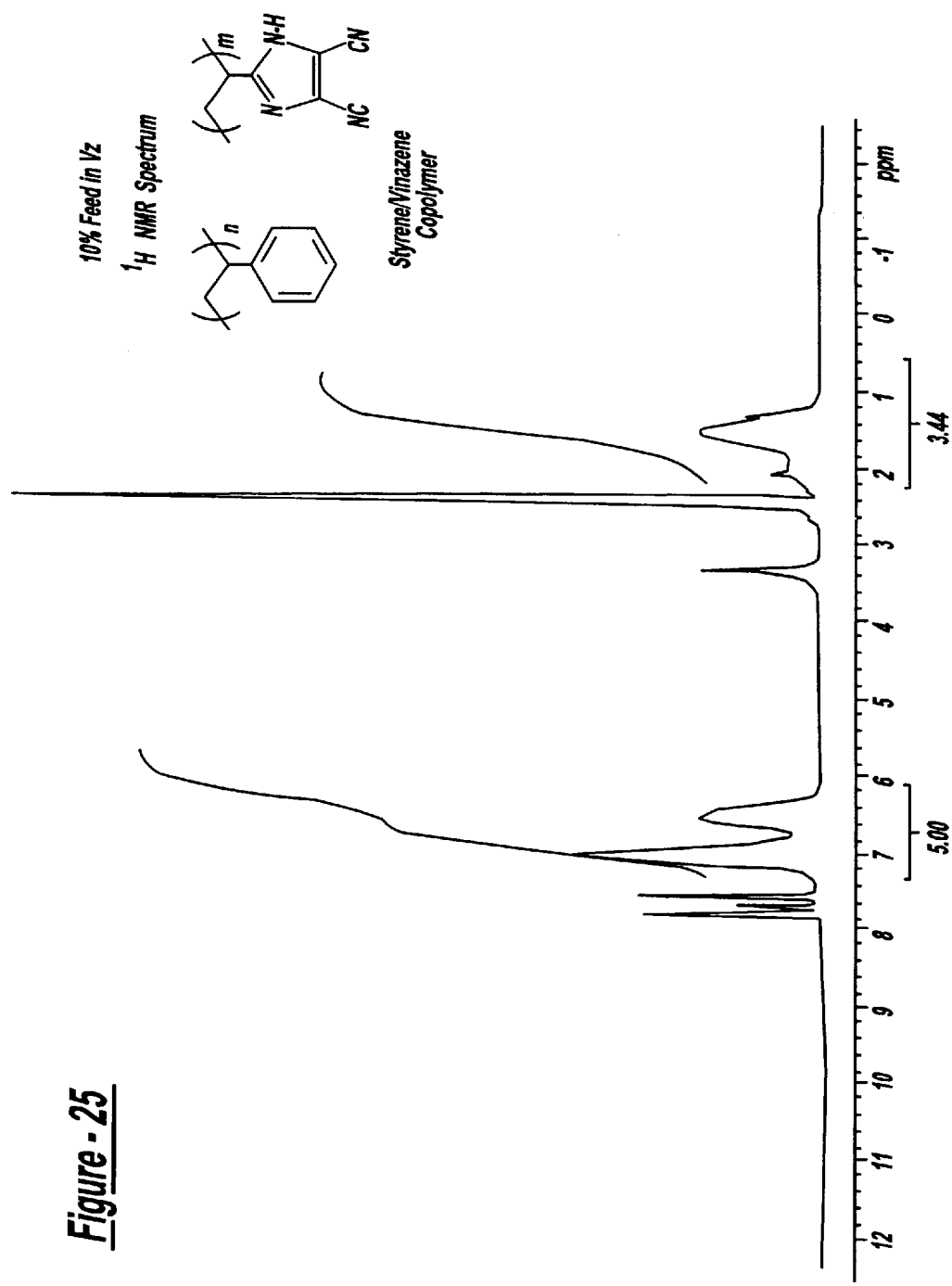
FIG. 25 is an NMR spectral analysis of the VINAZENE™/styrene copolymer prepared according to the present invention at 10% feed.

The preceding procedure was repeated with a 10% feed ratio for VINAZENE™ and styrene. Relevant NMR data are collected at FIG. 25.

As noted previously, 1-methyl-VINAZENE™ can be readily prepared from VINAZENE™. The 1-methyl-VINAZENE™ derivative can be polymerized by radical initiation to yield the polymethyl-VINAZENE™ homopolymer. Addition of the polymethyl-VINAZENE™ homopolymer to N-methylpyrrolidone (NMP) with the addition of equimolar or excess amounts of LiCl and heating to reflux demethylates the polymer. This polymer grafting reaction takes several hours to proceed to completion. If the reflux reaction is stopped before going to completion, a copolymer is effectively formed which could also be prepared by radical copolymerization of methyl-VINAZENE™ and VINAZENE™. However, the demethylization procedure advantageously provides an alternate approach which allows the use of various alkylated monomers in the synthesis step.

Use of the Novel Compounds in Oligomer Synthesis

Figure 26:
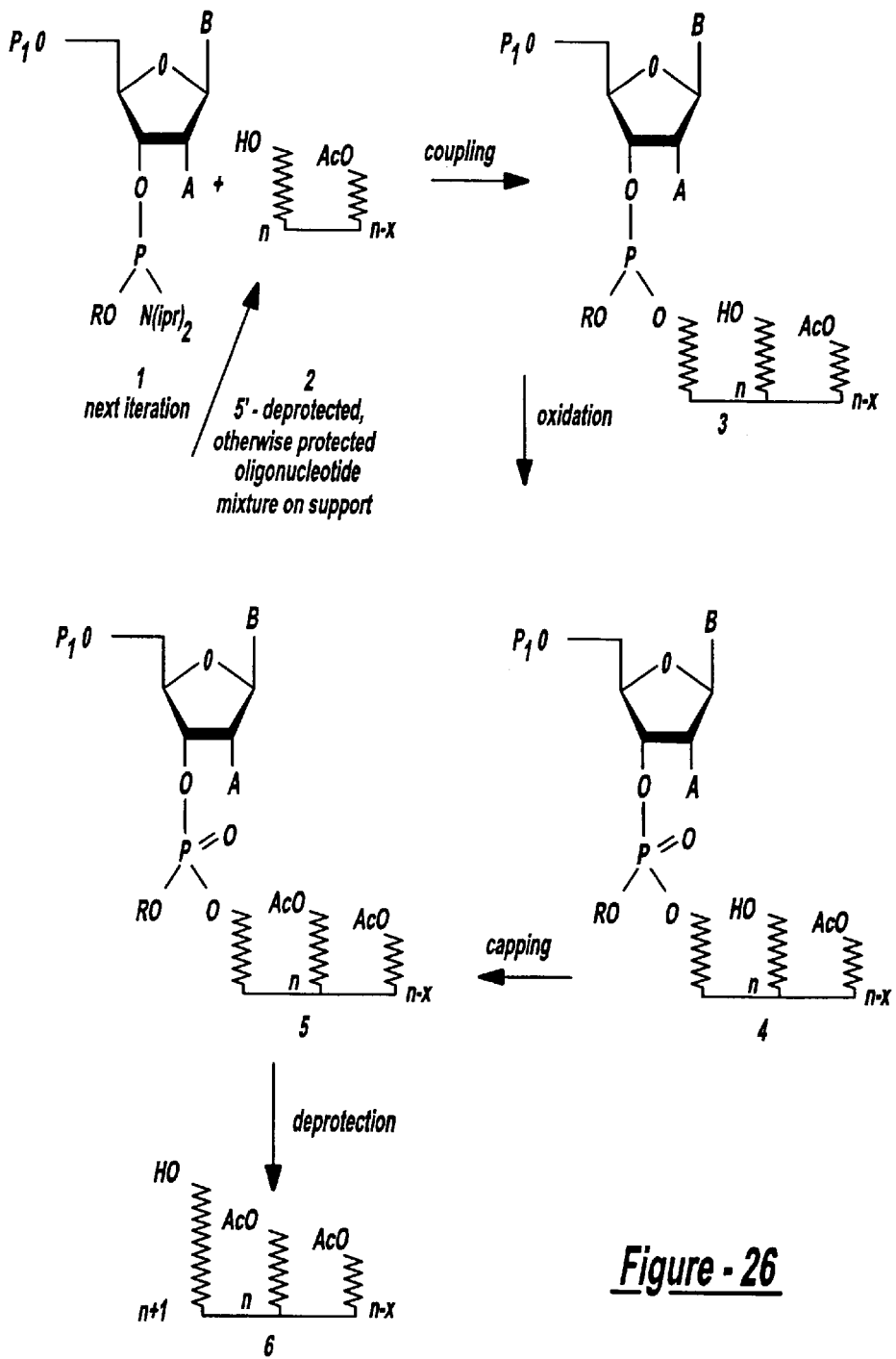
FIG. 26 is a schematic depiction of a reaction sequence for oligonocleotides.

The current state of the art in oligonucleotide synthesis is automated solid phase synthesis of oligonucleotides by the phosphoramidite method, which is illustrated in FIG. 26. (Beaucage and Iyer (1992) Tetrahedron 48:2223–2311; Zon and Geiser (1991) Anti-Cancer Drug Design 6:539–568: Matteucci and Caruthers (1981) J. Am. Chem. Soc. 103:3185–3191). General background for this technology using tetrazol condensing agent is also found in articles by M. H. Caruthers, Science, 1985, 281 and J. Chem. Ed., Vol. 66, No. 7, July, 1989, 577. Briefly, the 3'-terminal nucleoside of the oligonucleotide to be synthesized is attached to a solid support and the oligonucleotide is synthesized by addition of one nucleotide at a time while remaining attached to the support. As depicted in FIG. 26, a nucleoside monomer is protected ($P_1$) and the phosphoramidite is prepared (1). The phosphoramidite (referred to as the 5'-protected monomer unit) is then covalently attached to the growing oligonucleotide chain (2), via a phosphite triester linkage, through the 5'-hydroxy group of the ribose ring of the growing oligonucleotide chain to yield the oligonucleotide product (3), in which the majority of the growing oligonucleotide chain has been extended by one nucleotide. The product (3) is then oxidized to yield the phosphate triester (4). Prior to the addition of the next base to the growing nucleotide chain, the 5'-hydroxyl group must be deprotected. As can be seen in FIG. 26 (compound 4), however, not all of the reactive sites on the solid support react with the 5'-protected monomer. These unreacted sites (referred to as failure sequences) must, therefore, be protected (referred to as capping) (5) prior to deprotection of the 5'-hydroxyl group (6). Subsequent monomers, which have also been protected and converted to the phosphoramidite, are then sequentially added by coupling the 5'-end of the growing oligomer to the 3'-end of the monomer. Each coupling reaction extends the oligonucleotide by one monomer via a phosphite triester linkage. When the synthesis is complete, the desired oligonucleotide 6, the n+1 sequence, is deprotected and cleaved from the resin, together with all of the failure sequences (n, n–x).

In the most preferred embodiment of the invention, the monomer unit consists of a 5'-protected phosphoramidite or H-phosphonate, wherein the protecting group is a substituted trityl group, levulinic acid group or silyl ether group. The preferred substitution on the protecting group is a diene functionality, which can react, via a Diels-Alder reaction, with a solid support, such as a resin, membrane or polymer that has been derivatized with a dienophile. In this embodiment, the unreacted oligonucleotide starting material is separated from the reacted nucleotide product based on the selective or specific covalent reaction of the 5'-protecting group with a derivatized resin.

Certain terms used to describe the invention herein are defined as follows:

"Nucleoside" means either a deoxyribonucleoside or a ribonucleoside or any chemical modifications thereof. Modifications of the nucleosides include, but are not limited to, 2'-position sugar modifications, 5-position pyrimidine modifications, 8-position purine modifications, modifications at cytosine exocyclic amines, substitution of 5-bromouracil, and the like.

Figure 27:
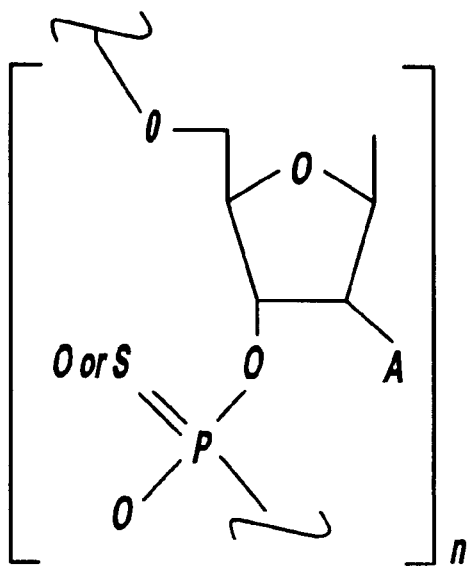
FIG. 27 shows a general structure of a representative oligonucleotide synthesized by a method according to the invention where the coupling agent is the polymer of the invention.

"Oligonucleotide" refers to either DNA or RNA or any chemical modifications thereof. The oligonucleotides synthesized by the method of this invention are depicted generally as in FIG. 27. In one embodiment, n=1 to 1,000, A is a 2'-sugar substituent, B is a nucleobase, and the phosphorous (P) is double bonded to oxygen (O) or sulfur (S).

A "solid support" as used herein refers to a resin, membrane, phase, polymer, polymer precursor, or soluble polymer that can undergo phase transition. A solid support also refers to a resin, membrane, phase, polymer, polymer precursor, or soluble polymer that has been derivatized.

Figure 28:
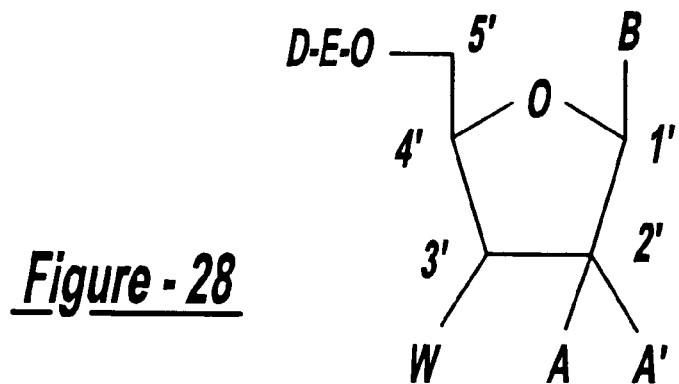
FIG. 28 shows a general structure of a 5'-protected monomer unit which is usable to form a block of oligonucleotides (growing nucleotide chain) prepared by synthesis methods of the invention.

Another example of "5'-protected monomer unit" is generally as in FIG. 28 including the conventional number for the ribose ring. In FIG. 28 is a nucleobase; A and A' are 2'-sugar substituents; W is independently selected from the group consisting of a phosphoramidite, H-phosphonate, phosphotriester, phosphoramidate, protected oligonucleotide and methyl-phosphonate; and D-E is an alcohol (hydroxyl) protecting group(s) which serves as an anchor for partitioning the successfully reacted oligonucleotide product away from the unreacted oligonucleotide starting material. In a preferred embodiment of the invention: W is a phosphoramidite or H-phosphonate; A and A' are in-dependently selected. (See PCT/US96/16668 (WO 97/14706 published Apr. 24, 1997) taking priority from U.S. Ser. No. 60/005,619 filed Oct. 17, 1996, "Method for Solution Phase Synthesis of Oligonucleotides", and PCT/IB96/01185 (WO 97/14710 published Apr. 24, 1997) taking priority from U.S. Ser. No. 08/546,198 filed Oct. 20, 1995, "Preparation of Phosphorothioate Oligomers", each of which is incorporate herein by reference in its entirety as a background teaching tool).

In another embodiment the 5'-deprotected oligonucleotide is not required to be attached to a support. Instead, a material is used to interact selectively with the 5-protecting group (D-E) of FIG. 28. For example, the product is captured or retained on a solid resin support by covalent reaction of the 5'-protecting group constituent with the resin. Then, unreacted starting material not carrying the 5'-protecting group is washed away.

"Starting material" as used herein refers to the compound that is reacted with the 5'-protected monomer unit during each cycle of synthesis to produce an oligomer that has been extended by one of more nucleotides. The starting material can be designed to produce a [5',3'] linkage between nucleotides or a [3',3'] linkage between nucleotides, depending on the desired oligonucleotide product. In the first instance, the starting material is a 5'-deprotected otherwise protected oligonucleotide of length n, in the second case the starting material is a 3'-deprotected otherwise protected oligonucleotide of length n, wherein n is an integer from 1–1000. The starting material is 2',3'-protected by protecting groups, such as base labile groups, that are compatible with the reaction of the 5'-protected monomer units with the starting material and with 5'-deprotection reactions. Additionally, because the process consists of the controlled and sequential polymerization of an oligonucleotide, the starting material of one cycle is typically the deprotected product from the previous cycle. Because in one embodiment, the process does not require that the 3'-terminal nucleotide be anchored to a solid support, the starting material can include non-nucleoside modifications. Non-nucleoside modifications can be introduced to the 3'-terminus which would not ordinarily be possible by solid phase synthesis. Non-nucleoside modifications to the 3'-terminus of the starting material include, but are not limited to, the use of polyethylene glycol monomethylether (molecular weight 5,000 to 100,000) (PEG) or other high molecular weight non-immunogenic units as the 3'-terminal monomer for preparation of oligonucleotides with improved pharmacokinetic properties.

"Product" as used herein refers to an oligonucleotide that is produced by the covalent reaction of the 5'-protected monomer unit with the starting material during each cycle. As stated above, if the starting material is a 5'-deprotected oligonucleotide of length n and the 5'-monomer unit is a single nucleotide, the product of the reaction will be a 5'-protected oligonucleotide of length n+1. If the 5'-protected monomer unit is an oligonucleotide block of length m, the product of the reaction will be a 5-protected oligonucleotide of length n+m. The product from a particular cycle is then 5'-deprotected and becomes the starting material for the next cycle.

A "failure sequence" refers to the starting material from a particular cycle that fails to react with the 5'-protected monomer unit during that cycle.

The growing oligonucleotide chain or block refers to either a 5'-deprotected oligonucleotide chain or a 5'-protected oligonucleotide chain that has been prepared by the sequential addition of nucleotides (N) beginning with the 3'-terminal nucleotide of the desired nucleotide using the method of this invention. After each reaction cycle of the process, the growing oligonucleotide increases in length by at least one oligonucleotide, and becomes the starting material for the next reaction cycle. As used herein, the term can refer to either starting material or product, and one of ordinary skill in the art will recognize what is intended by the term in a particular context.

In a representative synthesis method, a 5'-protected monomer unit, such as phosphoramidite, is added to a starting material in solution, in the presence of an activator, to yield a product to which one nucleotide has been added via a phosphite triester linkage. In a preferred embodiment, the activator is a polymer or copolymer according to the invention. The starting material is a 5'-deprotected otherwise protected oligonucleotide of length n, wherein n is an integer between 1 and 1000, and the product is a 5'-protected oligonucleotide of length n+1. The 5'-deprotected oligonucleotide starting material need not be anchored to a solid support, but rather, using standard methods, is simply 2', 3'-protected by protecting groups, such as base labile groups, that are compatible with the reaction of the 5'-protected monomer units with the starting material and with 5'-deprotection reactions. Thus, modifications can be introduced to the 3'-terminus which are not possible by solid phase synthesis. This includes, but it not limited to, the use of polyethylene glycol mono-methylether (molecular weight 5,000 to 100,000) or other high molecular weight non-immunogenic units.

After completion of the reaction between the 5'-protected monomer unit and starting material, the reaction mixture contains three species: unreacted 5-protected monomer unit, unreacted starting material, and the product of the reaction, compound, which is a 5'-protected olionucleotide of length n+1. As discussed above, any of the starting material (a 5'-deprotected oligonucleotide of length n) which fails to react with the 5'-protected monomer unit, is referred to as the failure sequence, as this sequence was not extended. The product of the reaction, compound, is a 5'-protected oligonucleotide chain extended by one nucleotide (length n+1), by the covalent reaction of the 5'-hydroxy group of starting material, an oligonucleotide of length n with the 3'-phosphoramidite group of the 5'-protected monomer unit. The product, compound, is the major component, and the 5'-protected monomer unit and the starting material that did not react are present only in minor amounts.

At this stage of the process, it is necessary to remove the unreacted 5'-protected monomer unit from the reaction mixture, both to purify the materials, and to recover the monomer starting material. According to this embodiment, non-reacted monomer is reacted to form an easily removable ionic species. Oxidation of the phosphite triester to phosphate triester may be carried out in the same reaction flask simply by addition of an oxidizing agent. In situ oxidation gives the desired oligonucleotide product, the phosphate salt of monomer, as well as unreacted oligonucleotide starting material. The monomer phosphate salt is the only free salt in the reaction mixture and thus is easily removed by techniques known to those in the art, including but not limited to, filtration through an anion exchange resin or membrane or extraction with an aqueous phase. In an alternate variation of this embodiment of the invention, the 3'-terminal monomer is a polyethylene glycol mono-methylether of molecular weight 5,000 to 100,000, preferably 20,000. In this case, a simply molecular weight cut-off membrane can be used to remove monomer. After the unreacted monomer has been removed from the reaction mixture, the remaining filtrate may then be partitioned in any manner suitable to separate the "oligonucleotide product" from the "failure sequence."

Example of Oligomer Synthesis

This example shows the utility of polymers and/or copolymers derived from 1-H-2-vinyl-4,5-dicyanoimidazole in promoting the phosphoramidite coupling reaction used in the laboratory synthesis of oligomers. The method of synthesis using the new activating agent of the invention will be exemplified by synthesis of DNA.

Figure 29:
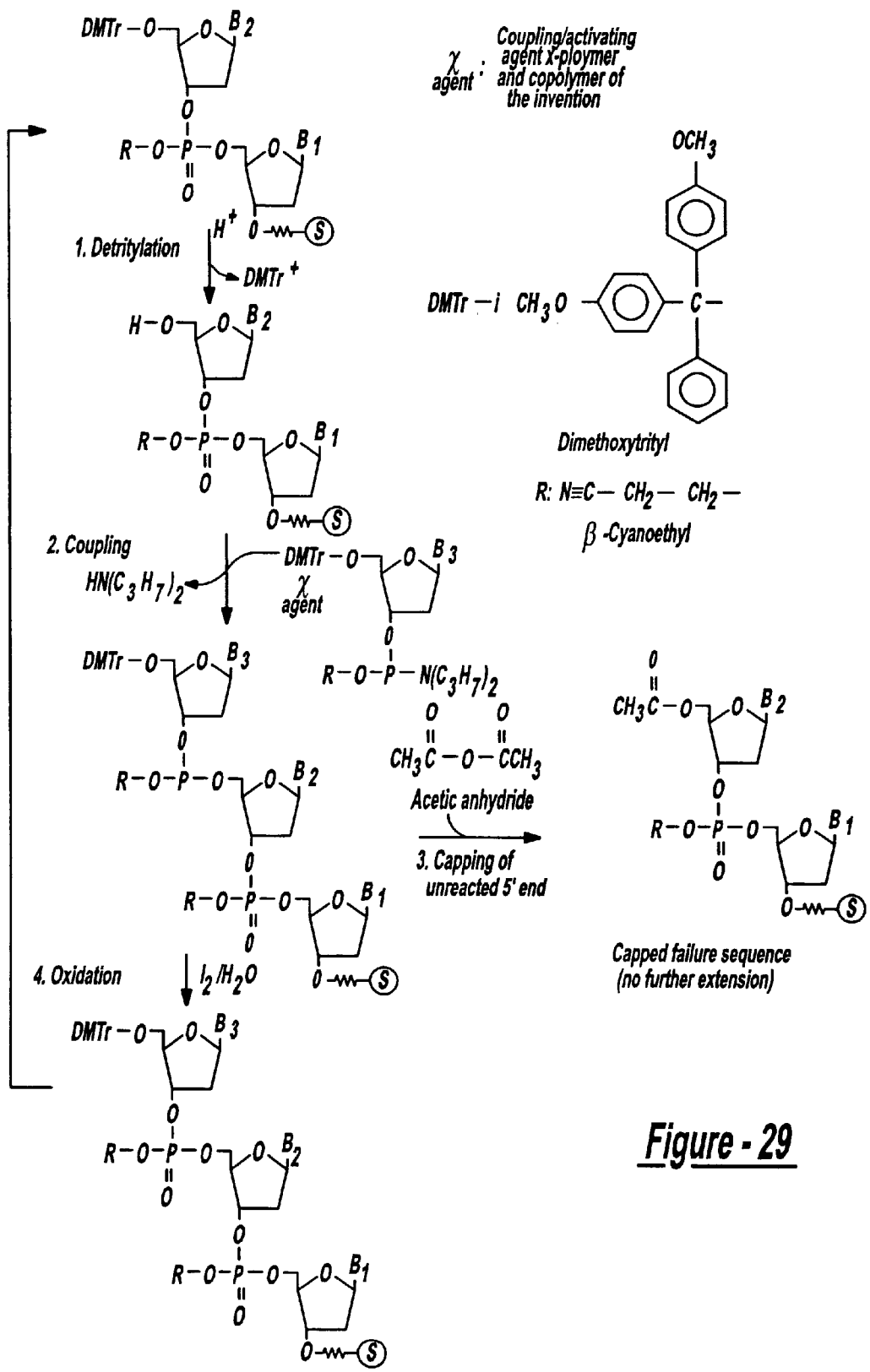
FIG. 29 shows a reaction sequence for synthesis of oligomers by the steps of detritylation; coupling; capping of unreacted material; and oxidation of coupled material. The coupling agent X of the invention is the polymer of the present invention.

The chemical synthesis of DNA which proceeds by cycles of addition of deoxymononucleotide, is shown in FIG. 29. FIG. 29 shows a reaction sequence for synthesis of oligomers by the steps of detritylation; coupling; capping of unreacted material; and oxidation of coupled material. The coupling/activating agent ($_x$) of the invention is shown with reference to the polymers and copolymers of the present invention. It is to be understood that suitable polymers and copolymers of the present invention as that term is used herein, preferably, are polymers of VINAZENE™ for which $R_1$=H and all copolymers for which the VINAZENE™ component for which $R_1$=H. Preferred among these are those copolymers which allow separation of the VINAZENE™substituents along the polymer backbone such as those mediated by free radical TEMPO. In this embodiment, a support is used, but is optional per embodiments described above. In step 1, detritylation of a support bound and protected nucleotide occurs, typically, by treatment with dichloroacetic acid in an inert solvent such as methylene chloride. The deprotected nucleotide is carefully washed and dried with acetonitrile.

In step 2, the deprotected nucleotide reacts with a protected doxynucleoside 3'-phosphoramidite. The synthesis proceeds in the presence of the preferred polymer activator. In one embodiment, the polymer activator is poly[1-(1H-4, 5-dicyano-2-imidazolyl) ethylene]. The polymer is added as a solid or on a support such as silica. The polymer condenses with the free 5'-hydroxyl, and then promotes the reaction of the phosphoramidate to effect coupling with the loss of isopropylamine. This salt is usually washed away in conventional methods absent the polymer activator of the invention. In the case of the polymer promoter/activator, a polymeric salt is formed. The polymeric salt can be removed by filtration and regenerated by treatment with strong acid, and used again.

Steps 3 and 4, the final two steps in the synthesis cycle, are capping and oxidation. The capping reaction, step 3, is carried out with acetic anhydride and dimethylaminopyridine, and its purpose is to acylate any DNA segments that fail to react during coupling. These unreacted oligomers, if not capped, might get involved in subsequent steps where their removal would be more difficult to achieve. The oxidation step uses $I_2$ in 2,6-lutidine/water/tetrahydrofuran (2:2:1 v/v/v) to convert the phosphite triester to the phosphate triester. After the sequential addition of nucleotides is completed, the DNA is freed of any remaining protecting groups, the beta-cyanoethyl protecting group on the phosphorous atoms is removed, and the ester linkage connecting the DNA to the support is hydrolyzed.

Note that the beta-cyanoethyl protecting group is a chiral auxiliary which has left- and right-handed features to aid in alignment of units to enhance chain formation. Such chiral auxiliary groups are known in the art for being hand-like mirror images that are not superimposable.

While this invention has been described in terms of certain embodiments thereof, it is not intended that it be limited to the above description, but rather only to the extent set forth in the following claims.

The embodiments of the invention in which an exclusive property or privilege is claimed are defined in the following claims:

What is claimed Is:

1. A copolymer comprising:
   a first compound repeat having units of the formula

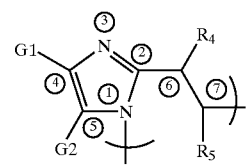

where R4 and R5 are each independently selected from the group consisting of hydrogen and substituted or unsubstituted alkyls having one to four carbon atoms; and where G1 and G2 are each independently selected from the group consisting of cyano, and substituents which replace cyano; and
   a second compound capable of polymerization with the first compound, the second compound capable of undergoing addition copolymerization.

2. The copolymer according to claim 1 wherein G1 and G2 are each cyano units.

3. The copolymer according to claim 1 wherein the substituted acrylate ester contains an alkyl group having one to ten carbon atoms and the acrylate has between three and five carbon atoms.

4. The copolymer comprising:
 a) repeat units of the formula:

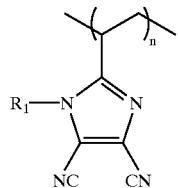

wherein R1 is characterized by being an organic substituent that does not interfere with polymerization; and b) repeating units of an addition polymer having monomeric units selected from the group consisting of styrene, isoprene, butadiene, acrylonitrile, and methyl methacrylate.

5. The copolymer of claim 4 wherein R1 is a substituted or unsubstituted alkyl having one to twelve carbon atoms.

6. The copolymer of claim 4 wherein R1 is selected from the group consisting of methyl, ethyl, propyl, isobutyl, benzyl, nonyl, and carbamoyl.

* * * * *